(12) United States Patent
Moffitt et al.

(10) Patent No.: US 11,944,823 B2
(45) Date of Patent: Apr. 2, 2024

(54) MULTI-MODE ELECTRICAL STIMULATION SYSTEMS AND METHODS OF MAKING AND USING

(71) Applicant: Boston Scientific Neuromodulation Corporation, Valencia, CA (US)

(72) Inventors: Michael A. Moffitt, Solon, OH (US); Stephen Carcieri, Los Angeles, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 179 days.

(21) Appl. No.: 17/684,042

(22) Filed: Mar. 1, 2022

(65) Prior Publication Data

US 2022/0266037 A1  Aug. 25, 2022

Related U.S. Application Data

(62) Division of application No. 16/396,230, filed on Apr. 26, 2019, now Pat. No. 11,298,553.

(60) Provisional application No. 62/663,908, filed on Apr. 27, 2018.

(51) Int. Cl.
*A61N 1/36* (2006.01)
*A61N 1/05* (2006.01)
*A61N 1/372* (2006.01)

(52) U.S. Cl.
CPC ......... *A61N 1/3727* (2013.01); *A61N 1/0534* (2013.01); *A61N 1/36071* (2013.01); *A61N 1/36132* (2013.01); *A61N 1/36135* (2013.01)

(58) Field of Classification Search
CPC ............ A61N 1/36132; A61N 1/36135; A61N 1/36185
See application file for complete search history.

(56) References Cited

U.S. PATENT DOCUMENTS

| | | | |
|---|---|---|---|
| 3,999,555 | A | 12/1976 | Person |
| 4,144,889 | A | 3/1979 | Tyers et al. |
| 4,177,818 | A | 12/1979 | De Pedro |
| 4,341,221 | A | 7/1982 | Testerman |

(Continued)

FOREIGN PATENT DOCUMENTS

| | | |
|---|---|---|
| EP | 1048320 | 11/2000 |
| EP | 1166819 | 1/2002 |

(Continued)

OTHER PUBLICATIONS

McIntyre, Cameron , et al., "Finite element analysis of the current-density and electric field generated by metal microelectrodes", Ann Biomed Eng . 29(3), (2001 ),227-235.

(Continued)

*Primary Examiner* — Eric D. Bertram
(74) *Attorney, Agent, or Firm* — Branch Partners PLLC; Bruce E. Black

(57) ABSTRACT

Methods and systems can facilitate identifying effective electrodes and other stimulation parameters, as well as determining whether to use cathodic and anodic stimulation. Alternately, the methods and systems may identify effective electrodes and other stimulation parameters based on preferential stimulation of different types of neural elements. These methods and systems can further facilitate programming an electrical stimulation system for stimulating patient tissue.

20 Claims, 7 Drawing Sheets

(56) References Cited

U.S. PATENT DOCUMENTS

| | | |
|---|---|---|
| 4,378,797 A | 4/1983 | Osterholm |
| 4,445,500 A | 5/1984 | Osterholm |
| 4,735,208 A | 4/1988 | Wyler et al. |
| 4,765,341 A | 8/1988 | Mower et al. |
| 4,841,973 A | 6/1989 | Stecker |
| 5,067,495 A | 11/1991 | Brehm |
| 5,099,846 A | 3/1992 | Hardy |
| 5,222,494 A | 6/1993 | Baker, Jr. |
| 5,255,693 A | 10/1993 | Dutcher |
| 5,259,387 A | 11/1993 | dePinto |
| 5,304,206 A | 4/1994 | Baker, Jr. et al. |
| 5,344,438 A | 9/1994 | Testerman et al. |
| 5,361,763 A | 11/1994 | Kao et al. |
| 5,452,407 A | 9/1995 | Crook |
| 5,560,360 A | 10/1996 | Filler et al. |
| 5,565,949 A | 10/1996 | Kasha, Jr. |
| 5,593,427 A | 1/1997 | Gliner et al. |
| 5,601,612 A | 2/1997 | Gliner et al. |
| 5,607,454 A | 3/1997 | Cameron et al. |
| 5,620,470 A | 4/1997 | Gliner et al. |
| 5,651,767 A | 7/1997 | Schulman |
| 5,711,316 A | 1/1998 | Elsberry et al. |
| 5,713,922 A | 2/1998 | King |
| 5,716,377 A | 2/1998 | Rise et al. |
| 5,724,985 A | 3/1998 | Snell et al. |
| 5,749,904 A | 5/1998 | Gliner et al. |
| 5,749,905 A | 5/1998 | Gliner et al. |
| 5,776,170 A | 7/1998 | MacDonald et al. |
| 5,782,762 A | 7/1998 | Vining |
| 5,843,148 A | 12/1998 | Gijsbers et al. |
| 5,859,922 A | 1/1999 | Hoffmann |
| 5,868,740 A | 2/1999 | LeVeen et al. |
| 5,897,583 A | 4/1999 | Meyer et al. |
| 5,910,804 A | 6/1999 | Fortenbery et al. |
| 5,925,070 A | 7/1999 | King et al. |
| 5,938,688 A | 8/1999 | Schiff |
| 5,938,690 A | 8/1999 | Aw et al. |
| 5,978,713 A | 11/1999 | Prutchi et al. |
| 6,016,449 A | 1/2000 | Fischell et al. |
| 6,029,090 A | 2/2000 | Herbst |
| 6,029,091 A | 2/2000 | de la Rama et al. |
| 6,050,992 A | 4/2000 | Nichols |
| 6,058,331 A | 5/2000 | King |
| 6,066,163 A | 5/2000 | John |
| 6,083,162 A | 7/2000 | Vining |
| 6,094,598 A | 7/2000 | Elsberry et al. |
| 6,096,756 A | 8/2000 | Crain et al. |
| 6,106,460 A | 8/2000 | Panescu et al. |
| 6,109,269 A | 8/2000 | Rise et al. |
| 6,128,538 A | 10/2000 | Fischell et al. |
| 6,129,685 A | 10/2000 | Howard, III |
| 6,146,390 A | 11/2000 | Heilbrun et al. |
| 6,161,044 A | 12/2000 | Silverstone |
| 6,167,311 A | 12/2000 | Rezai |
| 6,181,969 B1 | 1/2001 | Gord |
| 6,192,266 B1 | 2/2001 | Dupree et al. |
| 6,205,361 B1 | 3/2001 | Kuzma |
| 6,208,881 B1 | 3/2001 | Champeau |
| 6,240,308 B1 | 5/2001 | Hardy et al. |
| 6,246,912 B1 | 6/2001 | Sluijter et al. |
| 6,253,109 B1 | 6/2001 | Gielen |
| 6,289,239 B1 | 9/2001 | Panescu et al. |
| 6,301,492 B1 | 10/2001 | Zonenshayn |
| 6,310,619 B1 | 10/2001 | Rice |
| 6,319,241 B1 | 11/2001 | King |
| 6,336,899 B1 | 1/2002 | Yamazaki |
| 6,343,226 B1 | 1/2002 | Sunde et al. |
| 6,351,675 B1 | 2/2002 | Tholen et al. |
| 6,353,762 B1 | 3/2002 | Baudino et al. |
| 6,366,813 B1 | 4/2002 | Dilorenzo |
| 6,368,331 B1 | 4/2002 | Front et al. |
| 6,389,311 B1 | 5/2002 | Whayne et al. |
| 6,393,325 B1 | 5/2002 | Mann et al. |
| 6,421,566 B1 | 7/2002 | Holsheimer |
| 6,435,878 B1 | 8/2002 | Reynolds et al. |
| 6,442,432 B2 | 8/2002 | Lee |
| 6,463,328 B1 | 10/2002 | John |
| 6,491,699 B1 | 12/2002 | Henderson et al. |
| 6,494,831 B1 | 12/2002 | Koritzinsky |
| 6,507,759 B1 | 1/2003 | Prutchi et al. |
| 6,510,347 B2 | 1/2003 | Borkan |
| 6,516,227 B1 | 2/2003 | Meadows et al. |
| 6,517,480 B1 | 2/2003 | Krass |
| 6,539,263 B1 | 3/2003 | Schiff |
| 6,560,490 B2 | 5/2003 | Grill et al. |
| 6,579,280 B1 | 6/2003 | Kovach et al. |
| 6,600,956 B2 | 7/2003 | Maschino et al. |
| 6,606,523 B1 | 8/2003 | Jenkins |
| 6,609,029 B1 | 8/2003 | Mann et al. |
| 6,609,031 B1 | 8/2003 | Law et al. |
| 6,609,032 B1 | 8/2003 | Woods et al. |
| 6,622,048 B1 | 9/2003 | Mann et al. |
| 6,631,297 B1 | 10/2003 | Mo |
| 6,654,642 B2 | 11/2003 | North et al. |
| 6,662,053 B2 | 12/2003 | Borkan |
| 6,675,046 B2 | 1/2004 | Holsheimer |
| 6,684,106 B2 | 1/2004 | Herbst |
| 6,687,392 B1 | 2/2004 | Touzawa et al. |
| 6,690,972 B2 | 2/2004 | Conley et al. |
| 6,690,974 B2 | 2/2004 | Archer et al. |
| 6,692,315 B1 | 2/2004 | Soumillion et al. |
| 6,694,162 B2 | 2/2004 | Hartlep |
| 6,694,163 B1 | 2/2004 | Vining |
| 6,708,096 B1 | 3/2004 | Frei et al. |
| 6,741,892 B1 | 5/2004 | Meadows et al. |
| 6,748,098 B1 | 6/2004 | Rosenfeld |
| 6,748,276 B1 | 6/2004 | Daignault, Jr. et al. |
| 6,778,846 B1 | 8/2004 | Martinez et al. |
| 6,782,291 B1 * | 8/2004 | Bornzin ............ A61N 1/3686 607/28 |
| 6,788,969 B2 | 9/2004 | Dupree et al. |
| 6,795,737 B2 | 9/2004 | Gielen et al. |
| 6,827,681 B2 | 12/2004 | Tanner et al. |
| 6,830,544 B2 | 12/2004 | Tanner |
| 6,845,267 B2 | 1/2005 | Harrison et al. |
| 6,850,802 B2 | 2/2005 | Holsheimer |
| 6,895,280 B2 | 5/2005 | Meadows et al. |
| 6,909,913 B2 | 6/2005 | Vining |
| 6,937,891 B2 | 8/2005 | Leinders et al. |
| 6,937,903 B2 | 8/2005 | Schuler et al. |
| 6,944,497 B2 | 9/2005 | Stypulkowski |
| 6,944,501 B1 | 9/2005 | Pless |
| 6,950,707 B2 | 9/2005 | Whitehurst |
| 6,969,388 B2 | 11/2005 | Goldman et al. |
| 7,003,349 B1 | 2/2006 | Andersson et al. |
| 7,003,352 B1 | 2/2006 | Whitehurst |
| 7,008,370 B2 | 3/2006 | Tanner et al. |
| 7,008,413 B2 | 3/2006 | Kovach et al. |
| 7,035,690 B2 | 4/2006 | Goetz |
| 7,043,293 B1 | 5/2006 | Baura |
| 7,047,082 B1 | 5/2006 | Schrom et al. |
| 7,047,084 B2 | 5/2006 | Erickson et al. |
| 7,050,857 B2 | 5/2006 | Samuelsson et al. |
| 7,054,692 B1 | 5/2006 | Whitehurst et al. |
| 7,136,518 B2 | 5/2006 | Griffin et al. |
| 7,058,446 B2 | 6/2006 | Schuler et al. |
| 7,082,333 B1 | 7/2006 | Bauhahn et al. |
| 7,107,102 B2 | 9/2006 | Daignault et al. |
| 7,126,000 B2 | 10/2006 | Ogawa et al. |
| 7,127,297 B2 | 10/2006 | Law et al. |
| 7,136,695 B2 | 11/2006 | Pless et al. |
| 7,142,923 B2 | 11/2006 | North et al. |
| 7,146,219 B2 | 12/2006 | Sieracki et al. |
| 7,146,223 B1 | 12/2006 | King |
| 7,151,961 B1 | 12/2006 | Whitehurst |
| 7,155,279 B2 | 12/2006 | Whitehurst |
| 7,167,760 B2 | 1/2007 | Dawant et al. |
| 7,177,674 B2 | 2/2007 | Echauz et al. |
| 7,181,286 B2 | 2/2007 | Sieracki et al. |
| 7,184,837 B2 | 2/2007 | Goetz |
| 7,191,014 B2 | 3/2007 | Kobayashi et al. |
| 7,209,787 B2 | 4/2007 | Dilorenzo |
| 7,211,050 B1 | 5/2007 | Caplygin |
| 7,216,000 B2 | 5/2007 | Sieracki et al. |

(56) References Cited

U.S. PATENT DOCUMENTS

| | | |
|---|---|---|
| 7,217,276 B2 | 5/2007 | Henderson |
| 7,218,968 B2 | 5/2007 | Condie et al. |
| 7,228,179 B2 | 6/2007 | Campen et al. |
| 7,231,254 B2 | 6/2007 | DiLorenzo |
| 7,236,830 B2 | 6/2007 | Gliner |
| 7,239,910 B2 | 7/2007 | Tanner |
| 7,239,916 B2 | 7/2007 | Thompson et al. |
| 7,239,926 B2 | 7/2007 | Goetz |
| 7,242,984 B2 | 7/2007 | DiLorenzo |
| 7,244,150 B1 | 7/2007 | Brase et al. |
| 7,252,090 B2 | 8/2007 | Goetz |
| 7,254,445 B2 | 8/2007 | Aw et al. |
| 7,254,446 B1 | 8/2007 | Erickson |
| 7,257,447 B2 | 8/2007 | Cates et al. |
| 7,266,412 B2 | 9/2007 | Stypulkowski |
| 7,294,107 B2 | 11/2007 | Simon et al. |
| 7,295,876 B1 | 11/2007 | Erickson |
| 7,299,096 B2 | 11/2007 | Balzer et al. |
| 7,308,302 B1 | 12/2007 | Schuler et al. |
| 7,313,430 B2 | 12/2007 | Urquhart |
| 7,324,851 B1 | 1/2008 | DiLorenzo |
| 7,346,282 B2 | 3/2008 | Sakanaka et al. |
| 7,346,382 B2 | 3/2008 | McIntyre et al. |
| 7,388,974 B2 | 6/2008 | Yanagita |
| 7,437,193 B2 | 10/2008 | Parramon et al. |
| 7,450,997 B1 | 11/2008 | Pianca et al. |
| 7,463,928 B2 | 12/2008 | Lee et al. |
| 7,499,048 B2 | 3/2009 | Sieracki et al. |
| 7,505,815 B2 | 3/2009 | Lee et al. |
| 7,548,786 B2 | 6/2009 | Lee et al. |
| 7,565,199 B2 | 7/2009 | Sheffield et al. |
| 7,603,177 B2 | 10/2009 | Sieracki et al. |
| 7,617,002 B2 | 11/2009 | Goetz |
| 7,623,918 B2 | 11/2009 | Goetz |
| 7,650,184 B2 | 1/2010 | Walter |
| 7,657,319 B2 | 2/2010 | Goetz et al. |
| 7,672,734 B2 | 3/2010 | Anderson et al. |
| 7,676,273 B2 | 3/2010 | Goetz et al. |
| 7,680,526 B2 | 3/2010 | McIntyre et al. |
| 7,734,340 B2 | 6/2010 | De Ridder |
| 7,761,165 B1 | 7/2010 | He et al. |
| 7,783,359 B2 | 8/2010 | Meadows |
| 7,792,590 B1 | 9/2010 | Pianca et al. |
| 7,809,446 B2 | 10/2010 | Meadows |
| 7,826,902 B2 | 11/2010 | Stone et al. |
| 7,848,802 B2 | 12/2010 | Goetz et al. |
| 7,860,548 B2 | 12/2010 | McIntyre et al. |
| 7,904,134 B2 | 3/2011 | McIntyre et al. |
| 7,945,105 B1 | 5/2011 | Jaenisch |
| 7,949,395 B2 | 5/2011 | Kuzma |
| 7,974,706 B2 | 7/2011 | Moffitt et al. |
| 8,000,794 B2 | 8/2011 | Lozano |
| 8,019,439 B2 | 9/2011 | Kuzma et al. |
| 8,175,710 B2 | 5/2012 | He |
| 8,180,601 B2 | 5/2012 | Butson et al. |
| 8,195,300 B2 | 6/2012 | Gliner et al. |
| 8,209,027 B2 | 6/2012 | Butson et al. |
| 8,224,450 B2 | 7/2012 | Brase |
| 8,257,684 B2 | 9/2012 | Covalin et al. |
| 8,262,714 B2 | 9/2012 | Hulvershorn et al. |
| 8,271,094 B1 | 9/2012 | Moffitt et al. |
| 8,280,514 B2 | 10/2012 | Lozano et al. |
| 8,295,944 B2 | 10/2012 | Howard et al. |
| 8,326,433 B2 | 12/2012 | Blum et al. |
| 8,364,278 B2 | 1/2013 | Pianca et al. |
| 8,391,985 B2 | 3/2013 | McDonald |
| 8,429,174 B2 | 4/2013 | Ramani et al. |
| 8,452,415 B2 | 5/2013 | Goetz et al. |
| 8,473,061 B2 | 6/2013 | Moffitt et al. |
| 8,483,237 B2 | 7/2013 | Zimmermann et al. |
| 8,543,189 B2 | 9/2013 | Paitel et al. |
| 8,571,665 B2 | 10/2013 | Moffitt et al. |
| 8,589,316 B2 | 11/2013 | Lujan et al. |
| 8,594,800 B2 | 11/2013 | Butson et al. |
| 8,606,360 B2 | 12/2013 | Butson et al. |
| 8,620,452 B2 | 12/2013 | King et al. |
| 8,675,945 B2 | 3/2014 | Barnhorst et al. |
| 8,688,235 B1 | 4/2014 | Pianca et al. |
| 8,792,993 B2 | 7/2014 | Pianca et al. |
| 8,831,731 B2 | 9/2014 | Blum et al. |
| 8,849,632 B2 | 9/2014 | Sparks et al. |
| 8,958,615 B2 | 2/2015 | Blum et al. |
| 9,020,789 B2 | 4/2015 | Butson et al. |
| 9,050,470 B2 | 6/2015 | Carlton et al. |
| 9,072,905 B2 | 7/2015 | Kokones et al. |
| 9,248,272 B2 | 2/2016 | Romero |
| 9,623,250 B2 * | 4/2017 | Lee .................... A61N 1/36132 |
| 10,112,050 B2 | 10/2018 | Lee et al. |
| 10,335,547 B2 * | 7/2019 | Ward ................. A61N 1/36167 |
| 10,398,900 B2 | 9/2019 | Lee et al. |
| 2001/0031071 A1 | 10/2001 | Nichols et al. |
| 2002/0032375 A1 | 3/2002 | Bauch et al. |
| 2002/0062143 A1 | 5/2002 | Baudino et al. |
| 2002/0087201 A1 | 7/2002 | Firlik et al. |
| 2002/0099295 A1 | 7/2002 | Gil et al. |
| 2002/0115603 A1 | 8/2002 | Whitehouse |
| 2002/0116030 A1 | 8/2002 | Rezei |
| 2002/0123780 A1 | 9/2002 | Grill et al. |
| 2002/0128694 A1 | 9/2002 | Holsheimer |
| 2002/0151939 A1 | 10/2002 | Rezai |
| 2002/0183607 A1 | 12/2002 | Bauch et al. |
| 2002/0183740 A1 | 12/2002 | Edwards et al. |
| 2002/0183817 A1 | 12/2002 | Van Venrooij et al. |
| 2003/0097159 A1 | 5/2003 | Schiff et al. |
| 2003/0149450 A1 | 8/2003 | Mayberg |
| 2003/0171791 A1 | 9/2003 | KenKnight et al. |
| 2003/0212439 A1 | 11/2003 | Schuler et al. |
| 2004/0034394 A1 | 2/2004 | Woods et al. |
| 2004/0044279 A1 | 3/2004 | Lewin et al. |
| 2004/0044378 A1 | 3/2004 | Holsheimer |
| 2004/0044379 A1 | 3/2004 | Holsheimer |
| 2004/0054297 A1 | 3/2004 | Wingeier et al. |
| 2004/0059395 A1 | 3/2004 | North et al. |
| 2004/0106916 A1 | 6/2004 | Quaid et al. |
| 2004/0133248 A1 | 7/2004 | Frei et al. |
| 2004/0152957 A1 | 8/2004 | Stivoric et al. |
| 2004/0158298 A1 * | 8/2004 | Gliner ................ A61N 1/36021 607/48 |
| 2004/0181262 A1 | 9/2004 | Bauhahn |
| 2004/0186532 A1 | 9/2004 | Tadlock |
| 2004/0199216 A1 | 10/2004 | Lee et al. |
| 2004/0267330 A1 | 12/2004 | Lee et al. |
| 2005/0021090 A1 | 1/2005 | Schuler et al. |
| 2005/0033380 A1 | 2/2005 | Tanner et al. |
| 2005/0049649 A1 | 3/2005 | Luders et al. |
| 2005/0060001 A1 | 3/2005 | Singhal et al. |
| 2005/0060009 A1 | 3/2005 | Goetz |
| 2005/0070781 A1 | 3/2005 | Dawant et al. |
| 2005/0075689 A1 | 4/2005 | Toy et al. |
| 2005/0085714 A1 | 4/2005 | Foley et al. |
| 2005/0165294 A1 | 7/2005 | Weiss |
| 2005/0171587 A1 | 8/2005 | Daglow et al. |
| 2005/0228250 A1 | 10/2005 | Bitter et al. |
| 2005/0251061 A1 | 11/2005 | Schuler et al. |
| 2005/0261061 A1 | 11/2005 | Nguyen et al. |
| 2005/0261601 A1 | 11/2005 | Schuler et al. |
| 2005/0261747 A1 | 11/2005 | Schuler et al. |
| 2005/0267347 A1 | 12/2005 | Oster |
| 2005/0288732 A1 | 12/2005 | Schuler et al. |
| 2006/0004422 A1 | 1/2006 | De Ridder |
| 2006/0017749 A1 | 1/2006 | McIntyre et al. |
| 2006/0020292 A1 | 1/2006 | Goetz et al. |
| 2006/0069415 A1 | 3/2006 | Cameron et al. |
| 2006/0094951 A1 | 5/2006 | Dean et al. |
| 2006/0095088 A1 | 5/2006 | De Riddler |
| 2006/0155340 A1 | 7/2006 | Schuler et al. |
| 2006/0206169 A1 | 9/2006 | Schuler |
| 2006/0218007 A1 | 9/2006 | Bjorner et al. |
| 2006/0224189 A1 | 10/2006 | Schuler et al. |
| 2006/0235472 A1 | 10/2006 | Goetz et al. |
| 2006/0259079 A1 | 11/2006 | King |
| 2006/0259099 A1 | 11/2006 | Goetz et al. |
| 2007/0000372 A1 | 1/2007 | Rezai et al. |
| 2007/0017749 A1 | 1/2007 | Dold et al. |

(56) References Cited

U.S. PATENT DOCUMENTS

| | | |
|---|---|---|
| 2007/0027514 A1 | 2/2007 | Gerber |
| 2007/0043268 A1 | 2/2007 | Russell |
| 2007/0049817 A1 | 3/2007 | Preiss et al. |
| 2007/0067003 A1 | 3/2007 | Sanchez et al. |
| 2007/0078498 A1 | 4/2007 | Rezai et al. |
| 2007/0083104 A1 | 4/2007 | Butson et al. |
| 2007/0123953 A1 | 5/2007 | Lee et al. |
| 2007/0129769 A1 | 6/2007 | Bourget et al. |
| 2007/0135855 A1 | 6/2007 | Foshee et al. |
| 2007/0150036 A1 | 6/2007 | Anderson |
| 2007/0156186 A1 | 7/2007 | Lee et al. |
| 2007/0162086 A1 | 7/2007 | DiLorenzo |
| 2007/0162235 A1 | 7/2007 | Zhan et al. |
| 2007/0168004 A1 | 7/2007 | Walter |
| 2007/0168007 A1 | 7/2007 | Kuzma et al. |
| 2007/0185544 A1 | 8/2007 | Dawant et al. |
| 2007/0191887 A1 | 8/2007 | Schuler et al. |
| 2007/0191912 A1 | 8/2007 | Ficher et al. |
| 2007/0197891 A1 | 8/2007 | Shachar et al. |
| 2007/0203450 A1 | 8/2007 | Berry |
| 2007/0203532 A1 | 8/2007 | Tass et al. |
| 2007/0203537 A1 | 8/2007 | Goetz et al. |
| 2007/0203538 A1 | 8/2007 | Stone et al. |
| 2007/0203539 A1 | 8/2007 | Stone et al. |
| 2007/0203540 A1 | 8/2007 | Goetz et al. |
| 2007/0203541 A1 | 8/2007 | Goetz et al. |
| 2007/0203543 A1 | 8/2007 | Stone et al. |
| 2007/0203544 A1 | 8/2007 | Goetz et al. |
| 2007/0203545 A1 | 8/2007 | Stone et al. |
| 2007/0203546 A1 | 8/2007 | Stone et al. |
| 2007/0213789 A1 | 9/2007 | Nolan et al. |
| 2007/0213790 A1 | 9/2007 | Nolan et al. |
| 2007/0244519 A1 | 10/2007 | Keacher et al. |
| 2007/0245318 A1 | 10/2007 | Goetz et al. |
| 2007/0255321 A1 | 11/2007 | Gerber et al. |
| 2007/0255322 A1 | 11/2007 | Gerber et al. |
| 2007/0265664 A1 | 11/2007 | Gerber et al. |
| 2007/0276441 A1 | 11/2007 | Goetz |
| 2007/0282189 A1 | 12/2007 | Dan et al. |
| 2007/0288064 A1 | 12/2007 | Butson et al. |
| 2008/0027514 A1 | 1/2008 | DeMulling et al. |
| 2008/0039895 A1 | 2/2008 | Fowler et al. |
| 2008/0071150 A1 | 3/2008 | Miesel et al. |
| 2008/0081982 A1 | 4/2008 | Simon et al. |
| 2008/0086451 A1 | 4/2008 | Torres et al. |
| 2008/0103533 A1 | 5/2008 | Patel et al. |
| 2008/0114233 A1 | 5/2008 | McIntyre et al. |
| 2008/0114579 A1 | 5/2008 | McIntyre et al. |
| 2008/0123922 A1 | 5/2008 | Gielen et al. |
| 2008/0123923 A1 | 5/2008 | Gielen et al. |
| 2008/0133141 A1 | 6/2008 | Frost |
| 2008/0141217 A1 | 6/2008 | Goetz et al. |
| 2008/0154340 A1 | 6/2008 | Goetz et al. |
| 2008/0154341 A1 | 6/2008 | McIntyre et al. |
| 2008/0163097 A1 | 7/2008 | Goetz et al. |
| 2008/0183256 A1 | 7/2008 | Keacher |
| 2008/0188734 A1 | 8/2008 | Suryanarayanan et al. |
| 2008/0215118 A1 | 9/2008 | Goetz et al. |
| 2008/0227139 A1 | 9/2008 | Deisseroth et al. |
| 2008/0242950 A1 | 10/2008 | Jung et al. |
| 2008/0261165 A1 | 10/2008 | Steingart et al. |
| 2008/0269588 A1 | 10/2008 | Csavoy et al. |
| 2008/0300654 A1 | 12/2008 | Lambert et al. |
| 2008/0300797 A1 | 12/2008 | Tabibiazar et al. |
| 2009/0016491 A1 | 1/2009 | Li |
| 2009/0054950 A1 | 2/2009 | Stephens |
| 2009/0082640 A1 | 3/2009 | Kovach et al. |
| 2009/0082829 A1 | 3/2009 | Panken et al. |
| 2009/0112289 A1 | 4/2009 | Lee et al. |
| 2009/0118635 A1 | 5/2009 | Lujan et al. |
| 2009/0118786 A1 | 5/2009 | Meadows et al. |
| 2009/0149917 A1 | 6/2009 | Whitehurst et al. |
| 2009/0187222 A1 | 7/2009 | Barker |
| 2009/0196471 A1 | 8/2009 | Goetz et al. |
| 2009/0196472 A1 | 8/2009 | Goetz et al. |
| 2009/0198306 A1 | 8/2009 | Goetz et al. |
| 2009/0198354 A1 | 8/2009 | Wilson |
| 2009/0204192 A1 | 8/2009 | Carlton et al. |
| 2009/0208073 A1 | 8/2009 | McIntyre et al. |
| 2009/0210208 A1 | 8/2009 | McIntyre et al. |
| 2009/0242399 A1 | 10/2009 | Kamath et al. |
| 2009/0276008 A1 | 11/2009 | Lee et al. |
| 2009/0276021 A1 | 11/2009 | Meadows et al. |
| 2009/0281595 A1 | 11/2009 | King et al. |
| 2009/0281596 A1 | 11/2009 | King et al. |
| 2009/0287271 A1 | 11/2009 | Blum et al. |
| 2009/0287272 A1 | 11/2009 | Kokones et al. |
| 2009/0287273 A1 | 11/2009 | Carlton et al. |
| 2009/0287467 A1 | 11/2009 | Sparks et al. |
| 2009/0299164 A1 | 12/2009 | Singhal et al. |
| 2009/0299165 A1 | 12/2009 | Singhal et al. |
| 2009/0299380 A1 | 12/2009 | Singhal et al. |
| 2010/0010566 A1 | 1/2010 | Thacker et al. |
| 2010/0010646 A1 | 1/2010 | Drew et al. |
| 2010/0023103 A1 | 1/2010 | Elborno |
| 2010/0023130 A1 | 1/2010 | Henry et al. |
| 2010/0030312 A1 | 2/2010 | Shen |
| 2010/0049276 A1 | 2/2010 | Blum et al. |
| 2010/0049280 A1 | 2/2010 | Goetz |
| 2010/0064249 A1 | 3/2010 | Groetken |
| 2010/0076535 A1 | 3/2010 | Pianca et al. |
| 2010/0113959 A1 | 5/2010 | Pascual-Leon et al. |
| 2010/0121409 A1 | 5/2010 | Kothandaraman et al. |
| 2010/0135553 A1 | 6/2010 | Joglekar |
| 2010/0137944 A1 | 6/2010 | Zhu |
| 2010/0152604 A1 | 6/2010 | Kuala et al. |
| 2010/0179562 A1 | 7/2010 | Linker et al. |
| 2010/0268298 A1 | 10/2010 | Moffitt |
| 2010/0324410 A1 | 12/2010 | Paek et al. |
| 2010/0331883 A1 | 12/2010 | Schmitz et al. |
| 2011/0004267 A1 | 1/2011 | Meadows |
| 2011/0005069 A1 | 1/2011 | Pianca |
| 2011/0040351 A1 | 2/2011 | Buston et al. |
| 2011/0066407 A1 | 3/2011 | Butson et al. |
| 2011/0078900 A1 | 4/2011 | Pianca et al. |
| 2011/0093045 A1 | 4/2011 | Moffitt |
| 2011/0130803 A1 | 6/2011 | McDonald |
| 2011/0130816 A1 | 6/2011 | Howard et al. |
| 2011/0130817 A1 | 6/2011 | Chen |
| 2011/0130818 A1 | 6/2011 | Chen |
| 2011/0172737 A1 | 7/2011 | Davis et al. |
| 2011/0184487 A1 | 7/2011 | Alberts et al. |
| 2011/0191275 A1 | 8/2011 | Lujan et al. |
| 2011/0196253 A1 | 8/2011 | McIntyre et al. |
| 2011/0213440 A1 | 9/2011 | Fowler et al. |
| 2011/0238129 A1 | 9/2011 | Moffitt |
| 2011/0306845 A1 | 12/2011 | Osorio |
| 2011/0306846 A1 | 12/2011 | Osorio |
| 2011/0307032 A1 | 12/2011 | Goetz et al. |
| 2011/0313500 A1 | 12/2011 | Barker et al. |
| 2012/0016378 A1 | 1/2012 | Pianca et al. |
| 2012/0027272 A1 | 2/2012 | Akinyemi et al. |
| 2012/0046710 A1 | 2/2012 | Digiore et al. |
| 2012/0046715 A1 | 2/2012 | Moffitt et al. |
| 2012/0071949 A1 | 3/2012 | Pianca et al. |
| 2012/0078106 A1 | 3/2012 | Dentinger et al. |
| 2012/0089205 A1 | 4/2012 | Boyden et al. |
| 2012/0101552 A1 | 4/2012 | Lazarewicz et al. |
| 2012/0116476 A1 | 5/2012 | Kothandaraman |
| 2012/0165898 A1 | 6/2012 | Moffitt |
| 2012/0165901 A1 | 6/2012 | Zhu et al. |
| 2012/0165911 A1 | 6/2012 | Pianca |
| 2012/0197375 A1 | 8/2012 | Pianca et al. |
| 2012/0203316 A1 | 8/2012 | Moffitt et al. |
| 2012/0203320 A1 | 8/2012 | Digiore et al. |
| 2012/0203321 A1 | 8/2012 | Moffitt et al. |
| 2012/0207378 A1 | 8/2012 | Gupta et al. |
| 2012/0226138 A1 | 9/2012 | DeSalles et al. |
| 2012/0229468 A1 | 9/2012 | Lee et al. |
| 2012/0239115 A1 | 9/2012 | Lee |
| 2012/0265262 A1 | 10/2012 | Osorio |
| 2012/0265268 A1 | 10/2012 | Blum et al. |
| 2012/0302912 A1 | 11/2012 | Moffitt et al. |
| 2012/0303087 A1 | 11/2012 | Moffitt et al. |

(56) References Cited

U.S. PATENT DOCUMENTS

| | | |
|---|---|---|
| 2012/0314924 A1 | 12/2012 | Carlton et al. |
| 2012/0316615 A1 | 12/2012 | Digiore et al. |
| 2012/0316619 A1 | 12/2012 | Goetz et al. |
| 2012/0330622 A1 | 12/2012 | Butson et al. |
| 2013/0039550 A1 | 2/2013 | Blum et al. |
| 2013/0060305 A1 | 3/2013 | Bokil |
| 2013/0105071 A1 | 5/2013 | Digiore et al. |
| 2013/0116744 A1 | 5/2013 | Blum et al. |
| 2013/0116748 A1 | 5/2013 | Bokil et al. |
| 2013/0116749 A1 | 5/2013 | Carlton et al. |
| 2013/0116929 A1 | 5/2013 | Carlton et al. |
| 2013/0150922 A1 | 6/2013 | Butson et al. |
| 2013/0197424 A1 | 8/2013 | Bedenbaugh |
| 2013/0197602 A1 | 8/2013 | Pianca et al. |
| 2013/0261684 A1 | 10/2013 | Howard |
| 2013/0289380 A1 | 10/2013 | Molnar et al. |
| 2013/0317587 A1 | 11/2013 | Barker |
| 2013/0325091 A1 | 12/2013 | Pianca et al. |
| 2014/0039587 A1 | 2/2014 | Romero |
| 2014/0046397 A1* | 2/2014 | Rohrer ............... A61N 1/36185 607/40 |
| 2014/0066999 A1 | 3/2014 | Carcieri et al. |
| 2014/0067018 A1 | 3/2014 | Carcieri et al. |
| 2014/0067022 A1 | 3/2014 | Carcieri et al. |
| 2014/0107720 A1* | 4/2014 | Bornzin ............... A61N 1/3627 607/9 |
| 2014/0122379 A1 | 5/2014 | Moffitt et al. |
| 2014/0277284 A1 | 9/2014 | Chen et al. |
| 2014/0296953 A1 | 10/2014 | Pianca et al. |
| 2014/0343647 A1 | 11/2014 | Romero et al. |
| 2014/0353001 A1 | 12/2014 | Romero et al. |
| 2014/0358207 A1 | 12/2014 | Romero |
| 2014/0358208 A1 | 12/2014 | Howard et al. |
| 2014/0358209 A1 | 12/2014 | Romero et al. |
| 2014/0358210 A1 | 12/2014 | Howard et al. |
| 2015/0005842 A1 | 1/2015 | Lee et al. |
| 2015/0018915 A1 | 1/2015 | Leven |
| 2015/0021817 A1 | 1/2015 | Romero et al. |
| 2015/0045864 A1 | 2/2015 | Howard |
| 2015/0051681 A1 | 2/2015 | Hershey |
| 2015/0066111 A1 | 3/2015 | Blum et al. |
| 2015/0066120 A1 | 3/2015 | Govea |
| 2015/0134031 A1* | 5/2015 | Moffitt ............... A61N 1/37264 607/62 |
| 2015/0151113 A1 | 6/2015 | Govea et al. |
| 2015/0202448 A1* | 7/2015 | Hoffer ............... A61B 5/4893 607/42 |
| 2016/0001087 A1 | 1/2016 | Moffitt |
| 2016/0022994 A1* | 1/2016 | Moffitt ............... A61N 1/36132 607/46 |
| 2016/0022995 A1 | 1/2016 | Kothandaraman et al. |
| 2016/0023008 A1 | 1/2016 | Kothandaraman |
| 2016/0030749 A1 | 2/2016 | Carcieri et al. |
| 2016/0096025 A1 | 4/2016 | Moffitt et al. |
| 2016/0136429 A1 | 5/2016 | Massoumi et al. |
| 2016/0136443 A1 | 5/2016 | Kothandaraman et al. |
| 2016/0228692 A1 | 8/2016 | Steinke et al. |
| 2016/0256693 A1 | 9/2016 | Parramon |
| 2016/0375248 A1 | 12/2016 | Carcieri et al. |
| 2016/0375258 A1 | 12/2016 | Steinke |
| 2017/0100593 A1 | 4/2017 | Zottola |
| 2017/0100601 A1* | 4/2017 | Xiao ............... A61N 1/0534 |
| 2017/0106197 A1* | 4/2017 | Wechter et al. |
| 2017/0252570 A1 | 9/2017 | Serrano Carmona et al. |
| 2018/0110973 A1* | 4/2018 | Johnson ............... A61B 5/4836 |

FOREIGN PATENT DOCUMENTS

| | | |
|---|---|---|
| EP | 1372780 | 1/2004 |
| EP | 1559369 | 8/2005 |
| WO | 97/39797 | 10/1997 |
| WO | 98/48880 | 11/1998 |
| WO | 01/90876 | 11/2001 |
| WO | 02/26314 | 4/2002 |
| WO | 02/28473 | 4/2002 |
| WO | 02/065896 | 8/2002 |
| WO | 02/072192 | 9/2002 |
| WO | 03/086185 | 10/2003 |
| WO | 2004/019799 A2 | 3/2004 |
| WO | 2004041080 | 5/2005 |
| WO | 2006017053 | 2/2006 |
| WO | 2006113305 | 10/2006 |
| WO | 20071097859 | 8/2007 |
| WO | 20071097861 A1 | 8/2007 |
| WO | 2007/100427 | 9/2007 |
| WO | 2007/100428 | 9/2007 |
| WO | 2007/112061 | 10/2007 |
| WO | 2009097224 | 8/2009 |
| WO | 2010/006304 | 1/2010 |
| WO | 2010/120823 A2 | 10/2010 |
| WO | 2011025865 | 3/2011 |
| WO | 2011/139779 A1 | 11/2011 |
| WO | 2011/159688 A2 | 12/2011 |
| WO | 2012088482 | 6/2012 |
| WO | 2016/081099 | 5/2016 |

OTHER PUBLICATIONS

Foster, K. R., et al., "Dielectric properties of tissues and biological materials: a critical review.", Grit Rev Biomed Ena. 17(1 ). {1989),25-104.

Limousin, P., et al., "Electrical stimulation of the subthalamic nucleus in advanced Parkinson's disease", N Engl J Med .. 339(16), (Oct. 15, 1998), 1105-11.

Kitagawa, M., et al., "Two-year follow-up of chronic stimulation of the posterior subthalamic white matter for tremor-dominant Parkinson's disease.", Neurosurgery. 56(2). (Feb., 2005),281-9.

Johnson, M. D., et al., "Repeated voltage biasing improves unit recordings by reducing resistive tissue impedances", IEEE Transactions on Neural Systems and Rehabilitation Engineering, [see also IEEE Trans. on Rehabilitation Engineering (2005), 160-165.

Holsheimer, J., et al., "Chronaxie calculated from current-duration and voltage-duration data", J Neurosci Methods. 97(1). (Apr. 1, 2000),45-50.

Hines, M. L., et al., "The NEURON simulation environment", Neural Comput. 9(6). (Aug. 15, 1997), 1179-209.

Herzog, J., et al., "Most effective stimulation site in subthalamic deep brain stimulation for Parkinson's disease", Mov Disord. 19(9). (Sep. 2004),1050-4.

Hershey, T., et al., "Cortical and subcortical blood flow effects of subthalamic nucleus stimulation in PD.", Neurology 61(6). (Sep. 23, 2003),816-21.

Hemm, S., et al., "Evolution of Brain Impedance in Dystonic Patients Treated by GPi Electrical Stimulation", Neuromodulation 7(2) (Apr., 2004),67-75.

Hemm, S., et al., "Deep brain stimulation in movement disorders: stereotactic coregistration of two-dimensional electrical field modeling and magnetic resonance imaging.", J Neurosurg. 103(6): (Dec. 2005),949-55.

Haueisen, J, et al., "The influence of brain tissue anisotropy on human EEG and MEG", Neuroimage 15(1) (Jan. 2002),159-166.

Haslinger, B., et al., "Frequency-correlated decreases of motor cortex activity associated with subthalamic nucleus stimulation in Parkinson's disease.", Neuroimage 28(3). (Nov. 15, 2005),598-606.

Hashimoto, T., et al., "Stimulation of the subthalamic nucleus changes the firing pattern of pallidal neurons", J Neurosci. 23(5). (Mar. 1, 2003),1916-23.

Hardman, C. D., et al., "Comparison of the basal ganglia in rats, marmosets, macaques, baboons, and humans: volume and neuronal number for the output, internal relay, and striatal modulating nuclei", J Comp Neurol., 445(3). (Apr. 8, 2002),238-55.

McNaughtan et al., "Electrochemical Issues in Impedance Tomography", 1st World Congress on Industrial Process Tomography, Buxton, Greater Manchester, Apr. 14-17, 1999.

Grill, WM., et al., "Electrical properties of implant encapsulation tissue", Ann Biomed Eng. vol. 22. (1994),23-33.

(56) References Cited

OTHER PUBLICATIONS

Grill, W. M., et al., "Deep brain stimulation creates an informational lesion of the stimulated nucleus", Neuroreport. 15I7t (May 19, 2004 ), 1137-40.

Pulliam CL, Heldman DA, Orcutt TH, Mera TO, Giuffrida JP, Vitek JL. Motion sensor strategies for automated optimization of deep brain stimulation in Parkinson's disease. Parkinsonism Relat Disord. Apr. 2015; 21(4):378-82.

International Search Report and Written Opinion for PCT/US2019/029397 mailed Jun. 25, 2019.

Kirsch AD, Hassin-Baer S, Matthies C, Volkmann J, Steigerwald F. "Anodic versus cathodic neurostimulation of the subthalamic nucleus: A randomized-controlled study of acute clinical effects." Parkinsonism and Related Disorders 55 (2018) 61-67.

Official Communication for U.S. Appl. No. 16/396,230 mailed Feb. 2, 2021.

Official Communication for U.S. Appl. No. 16/396,230 mailed Apr. 19, 2021.

Official Communication for U.S. Appl. No. 16/396,230 mailed Jul. 26, 2021.

Official Communication for U.S. Appl. No. 16/396,230 mailed Oct. 29, 2021.

Alo, K. M., et al., "New trends in neuromodulation for the management of neuropathic pain," Neurosurgery, 50(4), (Apr. 2002), pp. 690-703, discussion pp. 703-704.

Ashby, P., et al., "Neurophysiological effects of stimulation through electrodes in the human subthalamic nucleus," Brain, 122 (PI 10), (Oct. 1999), pp. 1919-1931.

Baker, K. B., et al., "Subthalamic nucleus deep brain stimulus evoked potentials: Physiological and therapeutic Implications," Movement Disorders, 17(5), (Sep./Oct. 2002), pp. 969-983.

Bammer, R, et al., "Diffusion tensor imaging using single-shot SENSE-EPI", Magn Reson Med., 48(1 ), (Jul. 2002), pp. 128-136.

Basser, P J., et al., "MR diffusion tensor spectroscopy and imaging," Biophys J., 66(1 ), (Jan. 1994), pp. 259-267.

Basser, P J., et al., "New currents in electrical stimulation of excitable tissues," Annu Rev Biomed Eng., 2, (2000), pp. 377-397.

Benabid, AL., et al., "Chronic electrical stimulation of the ventralis intermedius nucleus of the thalamus as a treatment of movement disorders," J. Neurosurg., 84(2), (Feb. 1996), pp. 203-214.

Benabid, AL., et al., "Combined (Ihalamotoy and stimulation) stereotactic surgery of the VIM thalamic nucleus for bilateral Parkinson disease," Appl Neurophysiol, vol. 50, (1987), pp. 344-346.

Benabid, A L., et al., "Long-term suppression of tremor by chronic stimulation of the ventral intermediate thalamic nucleus," Lancet, 337 (8738), (Feb. 16, 1991 ), pp. 403-406.

Butson, C. R., et al., "Predicting the effects of deep brain stimulation with diffusion tensor based electric field models," Medical Image Computing and Computer-Assisted Intervention—Mic Cai 2006, Lecture Notes in Computer Science (LNCS), vol. 4191, pp. 429-437, LNCS, Springer, Berlin, DE.

Christensen, Gary E., et al., "Volumetric transformation of brain anatomy," IEEE Transactions on Medical Imaging, 16(6), (Dec. 1997), pp. 864-877.

Cooper, S , et al., "Differential effects of thalamic stimulation parameters on tremor and paresthesias in essential tremor," Movement Disorders, 17(Supp. 5), (2002), p. S193.

Coubes, P, et al., "Treatment of DYT1-generalised dystonia by stimulation of the internal globus pallidus," Lancet, 355 (9222), (Jun. 24, 2000), pp. 2220-2221.

Dasilva, A.F. M., et al., "A Primer Diffusion Tensor Imaging of Anatomical Substructures, " Neurosurg. Focus; 15(1) (Jul. 2003), pp. 1-4.

Dawant, B. M., et al., "Compuerized atlas-guided positioning of deep brain stimulators: a feasibility study," Biomedical Image registration, Second International Workshop, WBIR 2003, Revised Papers (Lecture notes in Comput. Sci. vol. (2717), Springer-Verlag Berlin, Germany(2003), pp. 142-150.

Finnis, K. W., et al., "3-D functional atlas of subcortical structures for image guided stereotactic neurosurgery," Neuroimage, vol. 9, No. 6, Iss. 2 (1999), p. S206.

Finnis, K. W., et al., "3D Functional Database of Subcorticol Structures for Surgical Guidance in Image Guided Stereotactic Neurosurgery," Medical Image Computing and Computer-Assisted Intervention—MICCAI'99, Second International Conference. Cambridge, UK, Sep. 19-22, 1999, Proceedings (1999), pp. 758-767.

Finnis, K. W., et al., "A 3-Dimensional Database of Deep Brain Functional Anatomy, and Its Application to Image-Guided Neurosurgery," Proceedings of the Third International Conference on Medical Image Computing and Computer-Assisted Intervention. Lecture Notes in Computer Science; vol. 1935 (2000), pp. 1-8.

Finnis, K. W., et al., "A functional database for guidance of surgical and therapeutic procedures in the deep brain," Proceedings of the 22nd Annual International Conference of the IEEE Engineering in Medicine and Biology Society, vol. 3 (2000), pp. 1787-1789.

Finnis, K. W., et al., "Application of a Population Based Electrophysiological Database to the Planning and Guidance of Deep Brain Stereotactic Neurosurgery," Proceedings of the 5th International Conference on Medical Image Computing and Computer-Assisted Intervention—Part 11, Lecture Notes In Computer Science; vol. 2489 (2002), pp. 69-76.

Finnis, K. W., et al., "Subcortical physiology deformed into a patient-specific brain atlas for image-guided stereotaxy," Proceedings of SPIE—vol. 4681 Medical Imaging 2002: Visualization, Image-Guided Procedures, and Display (May 2002), pp. 184-195.

Finnis, Krik W., et al., "Three-Dimensional Database of Subcortical Electrophysiology for Image-Guided Stereotatic Functional Neurosurgery," IEEE Transactions on Medical Imaging, 22(1) (Jan. 2003), pp. 93-104.

Gabriels, L , et al., "Deep brain stimulation for treatment-refractory obsessive-compulsive disorder: psychopathological and neuropsychological outcome in three cases," Acta Psychiatr Scand., 107(4) (2003), pp. 275-282.

Gabriels, LA., et al., "Long-term electrical capsular stimulation in patients with obsessive-compulsive disorder," Neurosurgery, 52(6) (Jun. 2003), pp. 1263-1276.

Goodall, E. V., et al., "Modeling study of activation and propagation delays during stimulation of peripheral nerve fibers with a tripolar cuff electrode," IEEE Transactions on Rehabilitation Engineering, [see also IEEE Trans. on Neural Systems and Rehabilitation], 3(3) (Sep. 1995), pp. 272-282.

Goodall, E. V., et al., "Position-selective activation of peripheral nerve fibers with a cuff electrode," IEEE Transactions on Biomedical Engineering, 43(8) (Aug. 1996), pp. 851-856.

Goodall, E. V., "Simulation of activation and propagation delay during tripolar neural stimulation," Proceedings of the 15th Annual International Conference of the IEEE Engineering in Medicine and Biology Society (1993), pp. 1203-1204.

Grill, WM., "Modeling the effects of electric fields on nerve fibers: influence of tissue electrical properties," IEEE Transactions on Biomedical Engineering, 46(8) (1999), pp. 918-928.

Grill, W. M., et al., "Neural and connective tissue response to long-term implantation of multiple contact nerve cuff electrodes," J Biomed Mater Res., 50(2) (May 2000), pp. 215-226.

Grill, W. M., "Neural modeling in neuromuscular and rehabilitation research," Proceedings of the 23rd Annual International Conference of the IEEE Engineering in Medicine and Biology Society, vol. 4 (2001 ), pp. 4065-4068.

Grill, W. M., et al., "Non-invasive measurement of the input-output properties of peripheral nerve stimulating electrodes," Journal of Neuroscience Methods, 65(1) (Mar. 1996), pp. 43-50.

Grill, W. M., et al., "Quantification of recruitment properties of multiple contact cuff electrodes," IEEE Transactions on Rehabilitation Engineering, [see also IEEE Trans. on Neural Systems and Rehabilitation], 4(2) (Jun. 1996), pp. 49-62.

Grill, W. M., "Spatially selective activation of peripheral nerve for neuroprosthetic applications," Ph.D. Case Western Reserve University, (1995), pp. 245 pages.

Grill, W. M., "Stability of the input-output properties of chronically implanted multiple contact nerve cuff stimulating electrodes," IEEE

(56) References Cited

OTHER PUBLICATIONS

Transactions on Rehabilitation Engineering [see also IEEE Trans. on Neural Systems and Rehabilitation] (1998), pp. 364-373.
Grill, W. M., "Stimulus waveforms for selective neural stimulation," IEEE Engineering in Medicine and Biology Magazine, 14(4) (Jul.-Aug. 1995), pp. 375-385.
Grill, W. M., et al., "Temporal stability of nerve cuff electrode recruitment properties," IEEE 17th Annual Conference Engineering in Medicine and Biology Society, vol. 2 (1995), pp. 1089-1090.
Gross, RE., et al., "Advances in neurostimulation for movement disorders," Neurol Res., 22(3) (Apr. 2000), pp. 247-258.
Guridi et al., "The subthalamic nucleus, hemiballismus and Parkinson's disease: reappraisal of a neurological dogma," Brain, vol. 124, 2001, pp. 5-19.
Haberler, C, et al., "No. tissue damage by chronic deep brain stimulation in Parkinson's disease," Ann Neurol., 48(3) (Sep. 2000), pp. 372-376.
Hamel, W, et al., "Deep brain stimulation of the subthalamic nucleus in Parkinson's disease: evaluation of active electrode contacts," J Neurol Neurosurg Psychiatry, 74(8) (Aug. 2003), pp. 1036-1046.
Hanekom, "Modelling encapsulation tissue around cochlear implant electrodes," Med. Biol. Eng. Comput. vol. 43 (2005), pp. 47-55.
Haueisen, J , et al., "The influence of brain tissue anisotropy on human EEG and MEG," Neuroimage, 15(1) (Jan. 2002), pp. 159-166.
D'Haese et al. Medical Image Computing and Computer-Assisted Intervention—MICCAI 2005 Lecture Notes in Computer Science, 2005, vol. 3750, 2005, 427-434.
Rohde et al. IEEE Transactions on Medical Imaging, vol. 22 No. 11, 2003 p. 1470-1479.
Dawant et al., Biomedical Image Registration. Lecture Notes in Computer Science, 2003, vol. 2717, 2003, 142-150.
Miocinovic et al., "Stereotactiv Neurosurgical Planning, Recording, and Visualization for Deep Brain Stimulation in Non-Human Primates", Journal of Neuroscience Methods, 162:32-41, Apr. 5, 2007, XP022021469.
Gemmar et al., "Advanced Methods for Target Navigation Using Microelectrode Recordings in Stereotactic Neurosurgery for Deep Brain Stimulation", 21st IEEE International Symposium on Computer-Based Medical Systems, Jun. 17, 2008, pp. 99-104, XP031284774.
Acar et al., "Safety Anterior Commissure-Posterior Commissure-Based Target Calculation of the Subthalamic Nucleus in Functional Stereotactic Procedures", Stereotactic Funct. Neurosura., 85:287-291, Aug. 2007.
Andrade-Souza, "Comparison of Three Methods of Targeting the Subthalamic Nucleus for Chronic Stimulation in Parkinson's Disease", Neurosurgery, 56:360-368, Apr. 2005.
Anheim et al., "Improvement in Parkinson Disease by Subthalamic Nucleus Stimulation Based on Electrode Placement", Arch Neural., 65:612-616, May 2008.
Zhang, Y., et al., "Atlas-guided tract reconstruction for automated and comprehensive examination of the white matter anatomy," Neuroimage 52(4) (2010), pp. 1289-1301.
""BioPSE" The Biomedical Problem Solving Environment", htt12:// www.sci.utah.edu/cibc/software/index.html, MCRR Center for Integrative Biomedical Computing,(2004).
Andrews, R. J., "Neuroprotection trek—the next generation: neuromodulation I. Techniques—deep brain stimulation, vagus nerve stimulation, and transcranial magnetic stimulation.", Ann NY Acad Sci. 993. (May 2003),1-13.
Carnevale, N.T. et al., "The Neuron Book," Cambridge, UK: Cambridge University Press (2006), 480 pages.
Chaturvedi: "Development of Accurate Computational Models for Patient-Specific Deep Brain Stimulation," Electronic Thesis or Dissertation, Jan. 2012, 162 pages.
Chaturvedi, A. et al.: "Patient-specific models of deep brain stimulation: Influence of field model complexity on neural activation predictions." Brain Stimulation, Elsevier, Amsterdam, NL, vol. 3, No. 2 Apr. 2010, pp. 65-77.

Frankemolle, et al., "Reversing cognitive-motor impairments in Parkinson's disease patients using a computational modeling approach to deep brain stimulation programming," Brian 133 (2010), pp. 746-761.
McIntyre, C.C., et al., "Modeling the excitablitity of mammalian nerve fibers: influence of afterpotentials on the recovery cycle," J Neurophysiol, 87(2) (Feb. 2002), pp. 995-1006.
Peterson, et al., "Predicting myelinated axon activation using spatial characteristics of the extracellular field," Journal of Neural Engineering, 8 (2011), 12 pages.
Warman, et al., "Modeling the Effects of Electric Fields on nerver Fibers; Dermination of Excitation Thresholds, "IEEE Transactions on Biomedical Engineering, vol. 39, No. 12 (Dec. 1992), pp. 1244-1254.
Wesselink, et al., "Analysis of Current Density and Related Parameters in Spinal Cord Stimulation," IEEE Transactions on Rehabilitation Engineering, vol. 6, No. Jun. 2, 1998, pp. 200-207.
Andrews, R. J., "Neuroprotection trek-the next generation: neuromodulation II. Applications—epilepsy, nerve regeneration, neurotrophins.", Ann NY Acad Sci. 993 (May 2003), 14-24.
Astrom, M. , et al., "The effect of cystic cavities on deep brain stimulation in the basal ganglia: a simulation-based study", J Neural Eng., 3(2), (Jun. 2006).132-8.
Bazin et al., "Free Software Tools for Atlas-based Volumetric Neuroimage Analysis", Proc. SPIE 5747, Medical Imaging 2005: Image Processing, 1824 May 5, 2005.
Back, C. , et al., "Postoperative Monitoring of the Electrical Properties of Tissue and Electrodes in Deep Brain Stimulation", Neuromodulation, 6(4), (Oct. 2003 ),248-253.
Baker, K. B., et al., "Evaluation of specific absorption rate as a dosimeter of MRI-related implant heating", J Magn Reson Imaging., 20(2), (Aug. 2004),315-20.
Brown, J. "Motor Cortex Stimulation," Neurosurgical Focus ( Sep. 15, 2001) 11(3):E5.
Budai et al., "Endogenous Opioid Peptides Acting at m-Opioid Receptors in the Dorsal Horn Contribute to Midbrain Modulation of Spinal Nociceptive Neurons, " Journal of Neurophysiology (1998) 79(2): 677-687.
Cesselin, F. "Opioid and anti-opioid peptides," Fundamental and Clinical Pharmacology (1995) 9(5): 409-33 (Abstract only).
Rezai et al., "Deep Brain Stimulation for Chronic Pain" Surgical Management of Pain, Chapter 44 pp. 565-576 (2002).
Xu, MD., Shi-Ang, article entitled "Comparison of Half-Band and Full-Band Electrodes for Intracochlear Electrical Stimulation", Annals of Otology, Rhinology & Laryngology (Annals of Head & Neck Medicine & Surgery), vol. 102(5) pp. 363-367 May 1993.
Bedard, C. , et al., "Modeling extracellular field potentials and the frequency-filtering properties of extracellular space", Biophys J .. 86(3). (Mar. 2004),1829-42.
Benabid, A. L., et al., "Future prospects of brain stimulation", Neurol Res.;22(3), (Apr. 2000), 237-46.
Brummer, S. B., et al., "Electrical Stimulation with Pt Electrodes: II—Estimation of Maximum Surface Redox (Theoretical Non-Gassing) Limits", IEEE Transactions on Biomedical Engineering, vol. BME-24, Issue 5, (Sep. 1977),440-443.
Butson, Christopher R., et al., "Deep Brain Stimulation of the Subthalamic Nucleus: Model-Based Analysis of the Effects of Electrode Capacitance on the Volume of Activation", Proceedings of the 2nd International IEEE EMBS, (Mar. 16-19, 2005),196-197.
Mcintyre, Cameron C., et al., "Cellular effects of deep brain stimulation: model-based analysis of activation and inhibition," J Neurophysiol, 91(4) (Apr. 2004), pp. 1457-1469.
Chaturvedi, A., et al., "Subthalamic Nucleus Deep Brain Stimulation: Accurate Axonal Threshold Prediction with Diffusion Tensor Based Electric Field Models", Engineering in Medicine and Biology Society, 2006. EMBS' 06 28th Annual International Conference of the IEEE, IEEE, Piscataway, NJ USA, Aug. 30, 2006.
Butson, Christopher et al., "Predicting the Effects of Deep Brain Stimulation with Diffusion Tensor Based Electric Field Models" Jan. 1, 2001, Medical Image Computing and Computer-Assisted Intervention-Mic CAI 2006 Lecture Notes in Computer Science; LNCS, Springer, Berlin, DE.

(56) References Cited

OTHER PUBLICATIONS

Butson, C. R., et al., "Deep brainstimulation interactive visualization system", Society for Neuroscience vol. 898.7 (2005).

Hodaie, M., et al., "Chronic anterior thalamus stimulation for intractable epilepsy," Epilepsia, 43(6) (Jun. 2002), pp. 603-608.

Hoekema, R., et al., "Multigrid solution of the potential field in modeling electrical nerve stimulation," Comput Biomed Res., 31(5) (Oct. 1998), pp. 348-362.

Holsheimer, J., et al., "Identification of the target neuronal elements in electrical deep brain stimulation," Eur J Neurosci., 12(12) (Dec. 2000), pp. 4573-4577.

Jezernik, S., et al., "Neural network classification of nerve activity recorded in a mixed nerve," Neurol Res., 23(5) (Jul. 2001), pp. 429-434.

Jones, DK., et al., "Optimal strategies for measuring diffusion in anisotropic systems by magnetic resonance imaging," Magn. Reson. Med., 42(3) (Sep. 1999), pp. 515-525.

Krack, P., et al., "Postoperative management of subthalamic nucleus stimulation for Parkinson's disease," Mov. Disord., vol. 17(suppl 3) (2002), pp. 188-197.

Le Bihan, D., et al., "Diffusion tensor imaging: concepts and applications," J Magn Reson Imaging, 13(4) (Apr. 2001), pp. 534-546.

Lee, D. C., et al., "Extracellular electrical stimulation of central neurons: quantitative studies," In: Handbook of neuroprosthetic methods, WE Finn and PG Lopresti (eds) CRC Press (2003), pp. 95-125.

Levy, AL., et al., "An Internet-connected, patient-specific, deformable brain atlas integrated into a surgical navigation system," J Digit Imaging, 10(3 Suppl 1) (Aug. 1997), pp. 231-237.

Liu, Haiying, et al., "Intra-operative MR-guided DBS implantation for treating PD and ET," Proceedings of SPIE vol. 4319, Department of Radiology & Neurosurgery, University of Minnesota, Minneapolis, MN 55455 (2001), pp. 272-276.

Mcintyre, C. C., et al., "Extracellular stimulation of central neurons: influence of stimulus waveform and frequency on neuronal output," J. Neurophysiol., 88(4), (Oct. 2002), pp. 1592-1604.

Mcintyre, C. C., et al., "Microstimulation of spinal motoneurons: a model study," Proceedings of the 19th Annual International Conference of the IEEE Engineering in Medicine and Biology society, vol. 5, (1997), pp. 2032-2034.

Mcintyre, Cameron C., et al., "Model-based Analysis of deep brain stimulation of the thalamus," Proceedings of the Second joint EMBS/BM ES Conference, vol. 3, Annual Fall Meeting of the Biomedical Engineering Society (Cal. No. 02CH37392) IEEEPiscataway, NJ (2002), pp. 2047-2048.

Mcintyre, C. C., et al., "Model-based design of stimulus trains for selective microstimulation of targeted neuronal populations," Proceedings of the 23rd Annual International Conference of the IEEE Engineering in Medicine and Biology Society, vol. 1 (2001), pp. 806-809.

Mcintyre, C. C., et al., Model-based design of stimulus waveforms for selective microstimulation in the central nervous system,, Proceedings of the First Joint [Engineering in Medicine and Biology, 1999. 21st Annual Conf. and the 1999 Annual FallMeeting of the Biomedical Engineering Soc.] BM ES/EMBS Conference, vol. 1 (1999), p. 384.

Mcintyre, Cameron C., et al., "Modeling the excitability of mammalian nerve fibers: influence of afterpotentials on the recovery cycle," J Neurophysiol, 87(2) (Feb. 2002), pp. 995-1006.

Mcintyre, Cameron C., et al., "Selective microstimulation of central nervous system neurons," Annals of biomedical engineering, 28(3) (Mar. 2000), pp. 219-233.

Mcintyre, C. C., et al., "Sensitivity analysis of a model of mammalian neural membrane," Biol Cybern., 79(1) (Jul. 1998), pp. 29-37.

Mcintyre, Cameron C., et al., "Uncovering the mechanism(s) of action of deep brain stimulation: activation, inhibition, or both," Clin Neurophysiol, 115(6) (Jun. 2004), pp. 1239-1248.

Mcintyre, Cameron C., et al., "Uncovering the mechanisms of deep brain stimulation for Parkinson's disease through functional imaging, neural recording, and neural modeling," Crit Rev Biomed Eng., 30(4-6) (2002), pp. 249-281.

Mouine et al. "Multi-Strategy and Multi-Algorithm Cochlear Prostheses", Biomed. Sci. Instrument, 2000; 36:233-238.

Nowinski, W. L., et al., "Statistical analysis of 168 bilateral subthalamic nucleus implantations by means of the probabilistic functional atlas.", Neurosurgery 57(4 Suppl) (Oct. 2005),319-30.

Obeso, J. A., et al., "Deep-brain stimulation of the subthalamic nucleus or the pars interna of the globus pallidus in Parkinson's disease.", N Engl J Med., 345{13I. The Deep-Brain Stimulation for Parkinson's Disease Study Group, (Sep. 27, 2001 ),956-63.

Butson et al.. "Current Steering to control the vol. of tissue activated during deep brain stimulation," vol. 1, No. 1, Dec. 3, 2007, pp. 7-15.

Patrick, S. K., et al., "Quantification of the UPDRS rigidity scale", IEEE Transactions on Neural Systems and Rehabilitation Engineering, [see also IEEE Trans. on Rehabilitation Engineering 9(1). (2001),31-41.

Phillips, M. D., et al., "Parkinson disease: pattern of functional MR imaging activation during deep brain stimulation of subthalamic nucleus—initial experience", Radiology 239(1). (Apr. 2006),209-16.

Ericsson, A. et al., "Construction of a patient-specific atlas of the brain: Application to normal aging," Biomedical Imaging: From Nano to Macro, ISBI 2008, 5th IEEE International Symposium, May 14, 2008, pp. 480-483.

Kaikai Shen et al., "Atlas selection strategy using least angle regression in multi-atlas segmentation propagation," Biomedical Imaging: From Nano to Macro, 2011, 8th IEEE International Symposium, ISBI 2011, Mar. 30, 2011, pp. 1746-1749.

Liliane Ramus et al., "Assessing selection methods in the cotnext of multi-atlas based segmentation," Biomedical Imaging: From Nano to Macro, 2010, IEEE International Symposium, Apr. 14, 2010, pp. 1321-1324.

Olivier Commowick et al., "Using Frankenstein's Creature Paradigm to Build a Patient Specific Atlas," Sep. 20, 2009, Medical Image Computing and Computer-Assisted Intervention, pp. 993-1000.

Lotjonen J.M.P. et al., "Fast and robust multi-atlas segmentation of brain magnetic resonance images," NeuroImage, Academic Press, vol. 49, No. 3, Feb. 1, 2010, pp. 2352-2365.

McIntyre, C. C., et al., "How does deep brain stimulation work? Present understanding and future questions.", J Clin Neurophysiol. 21 (1 ). (Jan.-Feb. 2004 ),40-50.

Sanchez Castro et al., "A cross validation study of deep brain stimulation targeting: From experts to Atlas-Based, Segmentation-Based and Automatic Registration Algorithms," IEEE Transactions on Medical Imaging, vol. 25, No. 11, Nov. 1, 2006, pp. 1440-1450.

Plaha, P., et al., "Stimulation of the caudal zona incerta is superior to stimulation of the subthalamic nucleus in improving contralateral parkinsonism.", Brain 129{Pt 7) (Jul. 2006), 1732-4 7.

Rattay, F, "Analysis of models for external stimulation of axons", IEEE Trans. Biomed. Eng. vol. 33 (1986),974-977.

Rattay, F., "Analysis of the electrical excitation of CNS neurons", IEEE Transactions on Biomedical Engineering 45(6). (Jun. 1998),766-772.

Rose, T. L., et al., "Electrical stimulation with Pt electrodes. VIII. Electrochemically safe charge injection limits with 0.2 ms pulses [neuronal application]", IEEE Transactions on Biomedical Engineering, 37(11 }, (Nov. 1990), 1118-1120.

Rubinstein, J. T., et al., "Signal coding in cochlear implants: exploiting stochastic effects of electrical stimulation", Ann Otol Rhinol Laryngol Suppl.. 191, (Sep. 2003), 14-9.

Schwan, H.P., et al., "The conductivity of living tissues.", Ann NY Acad Sci., 65(6). (AUQ., 1957),1007-13.

Taylor, R. S., et al., "Spinal cord stimulation for chronic back and leg pain and failed back surgery syndrome: a systematic review and analysis of prognostic factors", Spine 30(1 ). (Jan. 1, 2005), 152-60.

Siegel, Ralph M. et al., "Spatiotemporal dynamics of the functional architecture for gain fields in inferior parietal lobule of behaving monkey," Cerebral Cortex, New York, NY, vol. 17, No. 2, Feb. 2007, pp. 378-390.

(56) References Cited

OTHER PUBLICATIONS

Klein, A. et al., "Evaluation of 14 nonlinear deformation algorithms applied to human brain MRI registration," NeuroImage, Academic Press, Orlando, FL, vol. 46, No. 3, Jul. 2009, pp. 786-802.
Geddes, L. A., et al., "The specific resistance of biological material—a compendium of data for the biomedical engineer and physiologist.", Med Biol Ena. 5(3). (May 1967),271-93.
Gimsa, J., et al., "Choosing electrodes for deep brain stimulation experiments-electrochemical considerations.", J Neurosci Methods, 142(2), (Mar. 30, 2005),251-65.
Vidailhet, M., et al., "Bilateral deep-brain stimulation of the globus pallidus in primary generalized dystonia", N Engl J Med. 352(5) (Feb. 3, 2005),459-67.
Izad, Oliver, "Computationally Efficient Method in Predicating Axonal Excitation," Dissertation for Master Degree, Department of Biomedical Engineering, Case Western Reserve University, May 2009.
Jaccard, Paul, "Elude comparative de la distribution florale dans une portion odes Aples et des Jura," Bulletin de la Societe Vaudoise des Sciences Naturelles (1901), 37:547-579.
Dice, Lee R., "Measures of the Amount of Ecologic Association Between Species," Ecology 26(3) (1945): 297-302. doi:10.2307/1932409, http://jstor.org/stable/1932409.
Rand, WM., "Objective criteria for the evaluation of clustering methods," Journal of the American Statistical Association (American Statistical Association) 66 (336) (1971 ): 846-850, doi:10.2307/2284239, http://jstor.org/stable/2284239.
Hubert, Lawrence et al., "Comparing partitions," Journal of Classification 2(1) (1985): 193-218, doi:10.1007/BF01908075.
Cover, T.M. et al., "Elements of information theory," (1991) John Wiley & Sons, New York, NY.
Meila, Marina, "Comparing Clusterings by the Variation of Information," Learning Theory and Kernel Machines (2003):173-187.
Viola, P., et al., "Alignment by maximization of mutual information", International Journal of Com outer Vision 24(2). ( 1997), 137-154.
Butson et al. "StimExplorer: Deep Brain Stimulation Parameter Selection Software System," Acta Neurochirugica, Jan. 1, 2007, vol. 97, No. 2, pp. 569-574.
Butson et al. "Role of Electrode Design on the vol. of Tissue Activated During Deep Brain Stimulation," Journal of Neural Engineering, Mar. 1, 2006, vol. 3, No. 1, pp. 1-8.
Volkmann et al., Introduction to the Programming of Deep Brain Stimulators, Movement Disorders, vol. 17, Suppl. 3, pp. S181-S187 (2002).
Miocinovic et al. "Cicerone: Stereotactic Neurophysiological Recording and Deep Brain Stimulation Electrode Placement Software System," Acta Neurochirurgica Suppl., Jan. 1, 2007, vol. 97, No. 2, pp. 561-567.
Schmidt et al. "Sketching and Composing Widgets for 3D Manipulation," Eurographics, Apr. 2008, vol. 27, No. 2, pp. 301-310.
Volkmann, J., et al., "Basic algorithms for the programming of deep brain stimulation in Parkinson's disease", Mov Disord., 21 Suppl 14. (Jun. 2006),S284-9.
Walter, B. L., et al., "Surgical treatment for Parkinson's disease", Lancet Neural. 3(12). (Dec. 2004),719-28.
Wei, X. F., et al., "Current density distributions, field distributions and impedance analysis of segmented deep brain stimulation electrodes", J Neural Eng .. 2(4). (Dec. 2005), 139-47.
Zonenshayn, M., et al., "Location of the active contact within the subthalamic nucleus (STN) in the treatment of diopathic Parkinson's disease.", Surg Neurol., 62(3) (Sep. 2004),216-25.
Da Silva et al (A primer on diffusion tensor imaging of anatomical substructures. Neurosurg Focus 15(1): p. 1-4, Article 4, 2003.).
Micheli-Tzanakou, E., et al., "Computational Intelligence for target assesment in Parkinson's disease", Proceedings of SPIE vol. 4479. Applications and Science of Neural Networks, Fuzzy Systems, and Evolutionary Computation IV,(2001),54-69.

Grill, W. M., "Stimulus waveforms for selective neural stimulation", IEEE Engineering in Medicine and Biology Magazine, 14(4), (Jul.-Aug. 1995), 375-385.
Miocinovic, S., et al., "Sensitivity of temporal excitation properties to the neuronal element activated by extracellular stimulation", J Neurosci Methods. 132(1). (Jan. 15, 2004), 91-9.
Hunka, K. et al., Nursing Time to Program and Assess Deep Brain Stimulators in Movement Disorder Patients, J. Neursci Nurs., 37: 204-10 (Aug. 2005).
Moss, J., et al., "Electron microscopy of tissue adherent to explanted electrodes in dystonia and Parkinson's disease", Brain, 127{Pt 12). (Dec. 2004 ),2755-63.
Montgomery, E. B., et al., "Mechanisms of deep brain stimulation and future technical developments.", Neurol Res. 22(3). (Apr. 2000),259-66.
Merrill, D. R., et al., "Electrical stimulation of excitable tissue: design of efficacious and safe protocols", J Neurosci Methods. 141(2), (Feb. 15, 2005), 171-98.
Fisekovic et al., "New Controller for Functional Electrical Stimulation Systems", Med. Eng. Phys. 2001; 23:391-399.
Mcintyre, Cameron C., et al., "Electric Field and Stimulating Influence generated by Deep Brain Stimulation of the Subthalamaic Nucleus," Clinical Neurophysiology, 115(3) (Mar. 2004), pp. 589-595.
Mcintyre, Cameron C., et al., "Electric field generated by deep brain stimulation of the subthalamic nucleus," Biomedical Engineering Society Annual Meeting, Nashville TN (Oct. 2003), 16 pages.
Mcintyre, Cameron C., et al., "Excitation of central nervous system neurons by nonuniform electric fields," Biophys. J., 76(2) (1999), pp. 878-888.
McNeal, DR., et al., "Analysis of a model for excitation of myelinated nerve," IEEE Trans Biomed Eng., vol. 23 (1976), pp. 329-337.
Micheli-Tzanakou, E., et al., "Computational Intelligence for target assesment in Parkinson's disease," Proceedings of SPIE vol. 4479, Applications and Science of Neural Networks, Fuzzy Systems, and Evolutionary Computation IV (2001 ), pp. 54-69.
Miocinovic, S., et al., "Computational analysis of subthalamic nucleus and lenticular fasciculus activation during therapeutic deep brain stimulation," J Neurophysiol., 96(3) (Sep. 2006), pp. 1569-1580.
Miranda, P. C., et al., "The distribution of currents inducedin the brain by Magnetic Stimulation: a finite element analysis incorporating OT-MRI-derived conductivity data," Proc. Intl. Soc. Mag. Reson. Med. 9 (2001 ), p. 1540.
Miranda, P. C., et al., "The Electric Field Induced in the Brain by Magnetic Stimulation: A 3-D Finite-Element Analysis of the Effect of Tissue Heterogeneity and Anisotropy," IEEE Transactions on Biomedical Engineering, 50(9) (Sep. 2003), pp. 1074-1085.
Moffitt, MA., et al., "Prediction of myelinated nerve fiber stimulation thresholds: limitations of linear models," IEEE Transactions on Biomedical Engineering, 51 (2) (2003), pp. 229-236.
Moro, E, et al., "The impact on Parkinson's disease of electrical parameter settings in STN stimulation," Neurology, 59(5) (Sep. 10, 2002), pp. 706-713.
Nowak, LG., et al., "Axons, but not cell bodies, are activated by electrical stimulation in cortical gray matter. I. Evidence from chronaxie measurements," Exp. Brain Res., 118(4) (Feb. 1998), pp. 477-488.
Nowak, LG., et al., "Axons, but not cell bodies, are activated by electrical stimulation in cortical gray matter. II. Evidence from selective inactivation of cell bodies and axon initial segments," Exp. Brain Res., 118(4) (Feb. 1998), pp. 489-500.
O'Suilleabhain, PE., et al., "Tremor response to polarity, voltage, pulsewidth and frequency of thalamic stimulation," Neurology, 60(5) (Mar. 11, 2003), pp. 786-790.
Pierpaoli, C., et al., "Toward a quantitative assessment of diffusion anisotropy," Magn Reson Med., 36(6) (Dec. 1996), pp. 893-906.
Plonsey, R., et al., "Considerations of quasi-stationarity in electrophysiological systems, " Bull Math Biophys., 29(4) (Dec. 1967), pp. 657-664.
Ranck, J B., "Specific impedance of rabbit cerebral cortex," Exp. Neurol., vol. 7 (Feb. 1963), pp. 144-152.

(56) References Cited

OTHER PUBLICATIONS

Ranck, J B., et al., "The Specific impedance of the dorsal cols. of the cat: an anisotropic medium," Exp. Neurol., 11 (Apr. 1965), pp. 451-463.
Ranck, J B., "Which elements are excited in electrical stimulation of mammalian central nervous system: a review," Brain Res., 98(3) (Nov. 21, 1975), pp. 417-440.
Rattay, F., et al., "A model of the electrically excited human cochlear neuron. I. Contribution of neural substructures to the generation and propagation of spikes," Hear Res., 153(1-2) (Mar. 2001), pp. 43-63.
Rattay, F., "A model of the electrically excited human cochlear neuron. II. Influence of the three-dimensional cochlear structure on neural excitability," Hear Res., 153(1-2) (Mar. 2001), pp. 64-79.
Rattay, F., "Arrival at Functional Electrostimulation by modelling of fiber excitation," Proceedings of the Ninth annual Conference of the IEEE Engineering in Medicine and Biology Society (1987), pp. 1459-1460.
Rattay, F., "The influence of intrinsic noise can preserve the temporal fine structure of speech signals in models of electrically stimulated human cochlear neurones," Journal of Physiology, Scientific Meeting of the Physiological Society, London, England, UK Apr. 19-21, 1999 (Jul. 1999), p. 170P.
Rizzone, M., et al., "Deep brain stimulation of the subthalamic nucleus in Parkinson's disease: effects of variation in stimulation parameters," J. Neurol. Neurosurg. Psychiatry., 71(2) (Aug. 2001), pp. 215-219.
Saint-Cyr, J. A., et al., "Localization of clinically effective stimulating electrodes in the human subthalamic nucleus on magnetic resonance imaging," J. Neurosurg., 87(5) (Nov. 2002), pp. 1152-1166.
Sances, A., et al., "In Electroanesthesia: Biomedical and Biophysical Studies," A Sances and SJ Larson, Eds., Academic Press, NY (1975), pp. 114-124.
Sl. Jean, P., et al., "Automated atlas integration and interactive three-dimensional visualization tools for planning and guidance in functional neurosurgery," IEEE Transactions on Medical Imaging, 17(5) (1998), pp. 672-680.
Starr, P.A., et al., "Implantation of deep brain stimulators into the subthalamic nucleus: technical approach and magnetic resonance imaging-verified lead locations," J. Neurosurg., 97(2) (Aug. 2002), pp. 370-387.
Sterio, D., et al., "Neurophysiological refinement of subthalamic nucleus targeting," Neurosurgery, 50(1) (Jan. 2002), pp. 58-69.
Struijk, J. J., et al., "Excitation of dorsal root fibers in spinal cord stimulation: a theoretical study," IEEE Transactions on Biomedical Engineering, 40(7) (Jul. 1993), pp. 632-639.
Struijk, J J., et al., "Recruitment of dorsal col. fibers in spinal cord stimulation: influence of collateral branching," IEEE Transactions on Biomedical Engineering, 39(9) (Sep. 1992), pp. 903-912.
Tamma, F., et al., "Anatomo-clinical correlation of intraoperative stimulation-induced side effects during HF-DBS of the subthalamic nucleus," Neurol Sci., vol. 23 (Suppl 2) (2002), pp. 109-110.
Tarler, M., et al., "Comparison between monopolar and tripolar configurations in chronically implanted nerve cuff electrodes," IEEE 17th Annual Conference Engineering in Medicine and Biology Society, vol. 2 (1995), pp. 1093-1109.
Testerman, Roy L., "Coritical response to callosal stimulation: A model for determining safe and efficient stimulus parameters," Annals of Biomedical Engineering, 6(4) (1978), pp. 438-452.
Tuch, D.S., et al., "Conductivity mapping of biological tissue using diffusion MRI," Ann NY Acad Sci., 888 (Oct. 30, 1999), pp. 314-316.
Tuch, D.S., et al., "Conductivity tensor mapping of the human brain using diffusion tensor MRI," Proc Nall Acad Sci USA, 98(20) (Sep. 25, 2001), pp. 11697-11701.
Veraart, C., et al., "Selective control of muscle activation with a multipolar nerve cuff electrode," IEEE Transactions on Biomedical Engineering, 40(7) (Jul. 1993), pp. 640-653.

Vercueil, L., et al., "Deep brain stimulation in the treatment of severe dystonia," J. Neurol., 248(8) (Aug. 2001 ), pp. 695-700.
Vilalte, "Circuit Design of the Power-on-Reset," Apr. 2000, pp. 1-25.
Vitek, J. L., "Mechanisms of deep brain stimulation: excitation or inhibition," Mov. Disord., vol. 17 (Suppl. 3) (2002), pp. 69-72.
Voges, J., et al., "Bilateral high-frequency stimulation in the subthalamic nucleus for the treatment of Parkinson disease: correlation of therapeutic effect with anatomical electrode position," J. Neurosurg., 96(2) (Feb. 2002), pp. 269-279.
Wakana, S., et al., "Fiber tract-based atlas of human white matter anatomy," Radiology, 230(1) (Jan. 2004), pp. 77-87.
Alexander, DC., et al., "Spatial transformations of diffusion tensor magnetic resonance images," IEEE Transactions on Medical Imaging, 20 (11), (2001), pp. 1131-1139.
Wu, Y. R., et al., "Does Stimulation of the GPi control dyskinesia by activating inhibitory axons?," Mov. Disord., vol. 16 (2001), pp. 208-216.
Yelnik, J., et al., "Localization of stimulating electrodes in patients with Parkinson disease by using a three-dimensional atlas-magnetic resonance imaging coregistration method," J Neurosurg., 99(1) (Jul. 2003), pp. 89-99.
Yianni, John, et al., "Globus pallidus internus deep brain stimulation for dystonic conditions: a prospective audit," Mov. Disord., vol. 18 (2003), pp. 436-442.
Zonenshayn, M., et al., "Comparison of anatomic and neurophysiological methods for subthalamic nucleus targeting," Neurosurgery, 47(2) (Aug. 2000), pp. 282-294.
Voghell et al., "Programmable Current Source Dedicated to Implantable Microstimulators" ICM '98 Proceedings of the Tenth International Conference, pp. 67-70.
Butson, Christopher R., et al., "Patient-specific analysis of the vol. of tissue activated during deep brain stimulation", NeuroImage. vol. 34. (2007),661-670.
Adler, DE., et al., "The tentorial notch: anatomical variation, morphometric analysis, and classification in 100 human autopsy cases," J. Neurosurg., 96(6), (Jun. 2002), pp. 1103-1112.
Jones et al., "An Advanced Demultiplexing System for Physiological Stimulation", IEEE Transactions on Biomedical Engineering, vol. 44 No. 12 Dec. 1997, pp. 1210-1220.
Butson et al., "Tissue and Electrode Capacitance Reduce Neural Activation vols. During Deep Brain Stimulation", Clinical Neurophysiology, 116:2490-2500, Oct. 2005.
Butson et al., "Sources and Effects of Electrode Impedance During Deep Brain Stimulation", Clinical Neurophysiology, 117:44 7-454, Dec. 2005.
D'Haese et al., "Computer-Aided Placement of Deep Brain Stimulators: From Planning to Intraoperative Guidance", IEEE Transaction on Medical Imaging, 24:1469-1478, Nov. 2005.
Gross et al., "Electrophysiological Mapping for the Implantation of Deep Brain Stimulators for Parkinson's Disease and Tremor", Movement Disorders, 21 :S259-S283, Jun. 2006.
Halpern et al., "Brain Shift During Deep Brain Stimulation Surgery for Parkinson's Disease", Stereotact Funct. Neurosurg., 86:37-43, published online Sep. 2007.
Herzog et al., "Most Effective Stimulation Site in Subthalamic Deep Brain Stimulation for Parkinson's Disease", Movement Disorders, 19:1050-1099, published on line Mar. 2004.
Jeon et al., A Feasibility Study of Optical Coherence Tomography for Guiding Deep Brain Probes, Journal of Neuroscience Methods, 154:96-101, Jun. 2006.
Khan et al., "Assessment of Brain Shift Related to Deep Brain Stimulation Surgery", Sterreotact Funct. Neurosurg., 86:44-53, published online Sep. 2007.
Koop et al., "Improvement in a Quantitative Measure of Bradykinesia After Microelectrode Recording in Patients with Parkinson's Disease During Deep Brain Stimulation Surgery", Movement Disorders, 21 :673-678, published on line Jan. 2006.
Lemaire et al., "Brain Mapping in Stereotactic Surgery: A Brief Overview from the Probabilistic Targeting to the Patient-Based Anatomic Mapping", NeuroImage, 37:S109-S115, available online Jun. 2007.

(56) References Cited

OTHER PUBLICATIONS

Machado et al., "Deep Brain Stimulation for Parkinson's Disease: Surgical Technique and Perioperative Management", Movement Disorders, 21 :S247-S258, Jun. 2006.
Maks et al., "Deep Brain Stimulation Activation vols. and Their Association with Neurophysiological Mapping and Therapeutic Outcomes", Downloaded from jnnp.bmj.com, pp. 1-21, published online Apr. 2008.
Moran et al., "Real-Time Refinment of Subthalamic Nucleous Targeting Using Bayesian Decision-Making on the Root Mean Square Measure", Movement Disorders, 21: 1425-1431, published online Jun. 2006.
Sakamoto et al., "Homogeneous Fluorescence Assays for RNA Diagnosis by Pyrene-Conjugated 2'-0-Methyloligoribonucleotides", Nucleosides, Nucleotides, and Nucleric Acids, 26:1659-1664, on line publication Oct. 2007.
Winkler et al., The First Evaluation of Brain Shift During Functional Neurosurgery by Deformation Field Analysis, J. Neural. Neurosurg. Psychiatry, 76:1161-1163, Aug. 2005.
Yelnik et al., "A Three-Dimensional, Histological and Deformable Atlas of the Human Basal J Ganglia. I. Atlas Construction Based on Immunohistochemical and MRI Data", NeuroImage, 34:618,-638, Jan. 2007.
Ward, H. E., et al., "Update on deep brain stimulation for neuropsychiatric disorders," Neurobiol Dis 38 (3) (2010), pp. 346-353.
Alberts et al. "Bilateral subthalamic stimulation impairs cognitive-motor performance in Parkinson's disease patients." Brain (2008), 131, 3348-3360, Abstract.
Butson, Christopher R., et al., "Sources and effects of electrode impedance during deep brain stimulation", Clinical Neurophysiology. vol. 117.(2006),447-454.
An, et al., "Prefrontal cortical projections to longitudinal cols. in the midbrain periaqueductal gray in macaque monkeys," J Comp Neural 401 (4) (1998), pp. 455-479.
Bulson, C. R., et al., "Tissue and electrode capacitance reduce neural activation volumes during deep brain stimulation," Clinical Neurophysiology, vol. 116 (2005), pp. 2490-2500.
Carmichael, S. T., et al., "Connectional networks within the orbital and medial prefrontal cortex of macaque monkeys," J Comp Neural 371 (2) (1996), pp. 179-207.
Croxson, et al., "Quantitative investigation of connections of the prefrontal cortex in the human and macaque using probabilistic diffusion tractography," J Neurosci 25 (39) (2005), pp. 8854-8866.
Frankemolle, et al., "Reversing cognitive-motor impairments in Parkinson's disease patients using a computational modelling approach to deep brain stimulation programming," Brain 133 (2010), pp. 746-761.
Freedman, et al., "Subcortical projections of area 25 (subgenual cortex) of the macaque monkey," J Comp Neurol 421 (2) (2000), pp. 172-188.
Giacobbe, et al., "Treatment resistant depression as a failure of brain homeostatic mechanisms: implications for deep brain stimulation," Exp Neural 219 (1) (2009), pp. 44-52.
Goodman, et al., "Deep brain stimulation for intractable obsessive compulsive disorder: pilot study using a blinded, staggered-onset design," Biol Psychiatry 67 (6) (2010), pp. 535-542.
Greenberg, et al., "Deep brain stimulation of the ventral internal capsule/ventral striatum for obsessive-compulsive disorder: worldwide experience," Mol Psychiatry 15 (1) (2010), pp. 64-79.
Greenberg et al., "Three-year outcomes in deep brain stimulation for highly resistant obsessive-compulsive disorder," Neuropsychopharmacology 31 (11) (2006), pp. 2384-2393.
Gutman, et al., "A tractography analysis of two deep brain stimulation white matter targets for depression," Biol Psychiatry 65 (4) (2009), pp. 276-282.
Haber, et al., "Reward-related cortical inputs define a large striatal region in primates that interface with associative cortical connections, providing a substrate for incentive-based learning," J Neurosci 26 (32) (2006), pp. 8368-8376.
Haber, et al., "Cognitive and limbic circuits that are affected by deep brain stimulation," Front Biosci 14 (2009), pp. 1823-1834.
Hines, M. L., et al., "The NEURON simulation environment," Neural Comput., 9(6) (Aug. 15, 1997), pp. 1179-1209.
Hua, et al., "Tract probability maps in stereotaxic spaces: analyses of white matter anatomy and tract-specific quantification," Neuroimage 39 (1) (2008), pp. 336-347.
Johansen-Berg, et al., "Anatomical connectivity of the subgenual cingulate region targeted with deep brain stimulation for treatment-resistant depression," Cereb Cortex 18 (6) (2008), pp. 1374-1383.
Kopell, et al., "Deep brain stimulation for psychiatric disorders," J Clin Neurophysiol 21 (1) (2004), pp. 51-67.
Lozano, et al., "Subcallosal cingulate gyrus deep brain stimulation for treatment-resistant depression," Biol Psychiatry 64 (6) (2008), pp. 461-467.
Lujan, et al., "Tracking the mechanisms of deep brain stimulation for neuropsychiatric disorders," Front Biosci 13 (2008), pp. 5892-5904.
Lujan, J.L. et al., "Automated 3-Dimensional Brain Atlas Fitting to Microelectrode Recordings from Deep Brain Stimulation Surgeries," Stereotact. Fune !. Neurosurg. 87(2009), pp. 229-240.
Machado. et al., "Functional topography of the ventral striatum and anterior limb of the internal capsule determined by electrical stimulation of awake patients," Clin Neurophysiol 120 (11) (2009), pp. 1941-1948.
Malone, et al., "Deep brain stimulation of the ventral capsule/ventral striatum for treatment-resistant depression," Biol Psychiatry 65 (4) (2009), pp. 267-275.
Mayberg, H. S., et al., "Deep brain stimulation for treatment-resistant depression," Neuron, 45(5) (Mar. 3, 2005), pp. 651-660.
Mayberg, H. S., et al., "Limbic-cortical dysregulation: a proposed model of depression," J Neuropsychiatry Clin Neurosci. 9 (3) (1997), pp. 471-481.
McIntyre, C. C., et al., "Network perspectives on the mechanisms of deep brain stimulation," Neurobiol Dis 38 (3) (2010), pp. 329-337.
Miocinovic, S., et al., "Experimental and theoretical characterization of the voltage distribution generated by deep brain stimulation," Exp Neurol 216 (i) (2009), pp. 166-176.
Nuttin, et al., "Electrical stimulation in anterior limbs of internal capsules in patients with obsessive-compulsive disorder," Lancet 354 (9189) (1999), p. 1526.
Saxena, et al., "Cerebral glucose metabolism in obsessive-compulsive hoarding," Am J Psychiatry. 161 (6) (2004), pp. 1038-1048.
Viola, et al., "Importance-driven focus of attention," IEEE Trans Vis Comput Graph 12 (5) (2006), pp. 933-940.
Wakana, S., et al., "Reproducibility of quantitative tractography methods applied to cerebral white matter," Neuroimage 36 (3) (2007), pp. 630-644.
Mayr et al., "Basic Design and Construction of the Vienna FES Implants: Existing Solutions and Prospects for New Generations of Implants", Medical Engineering & Physics, 2001; 23:53-60.

* cited by examiner

MULTI-MODE ELECTRICAL STIMULATION SYSTEMS AND METHODS OF MAKING AND USING

CROSS-REFERENCE TO RELATED APPLICATIONS

This application is a divisional of U.S. patent application Ser. No. 16/396,230, filed Apr. 26, 2019, which issued as U.S. Pat. No. 11,298,553, which claims the benefit under 35 U.S.C. § 119(e) of U.S. Provisional Patent Application Ser. No. 62/663,908, filed Apr. 27, 2018, both of which are incorporated herein by reference.

FIELD

The present disclosure is directed to the area of implantable electrical stimulation systems and methods of making and using the systems. The present disclosure is also directed to electrical stimulation systems with multiple modes, such as anodic or cathodic stimulation modes, and methods of making and using.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients. Stimulation of the brain, such as deep brain stimulation, can be used to treat a variety of diseases or disorders.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

One aspect is a system for programming electrical stimulation of a patient using an implantable electrical stimulation system including an implantable pulse generator and a lead having a plurality of electrodes. The system includes a processor configured to receive a first response for each of a plurality of first monopolar stimulations performed using a subset of one or more of the electrodes of the lead as a cathode for each of the first monopolar stimulations; select a first subset of one or more of the electrodes based on the first responses; receive a second response for each of a plurality of second monopolar stimulations performed using a subset of one or more of the electrodes of the lead as an anode for each of the second monopolar stimulations; select a second subset of one or more of the electrodes based on the second responses; select a programming subset of one or more of the electrodes based, at least in part, on the responses associated with the first subset and second subset; receive a third response for each of a plurality of third monopolar stimulations performed using the programming subset with each of the third monopolar stimulation having a different stimulation amplitude; select a programming stimulation amplitude based on the third responses; receive direction to program the implantable pulse generator with the programming subset of one or more of the electrodes and the programming stimulation amplitude; and initiate a signal that provides the implantable pulse generator of the electrical stimulation system with the programming subset of one or more of the electrodes and the programming stimulation amplitude for generating electrical stimulation for the patient through the electrodes of the lead.

Another aspect is a method for programming electrical stimulation of a patient using an implantable electrical stimulation system including an implantable pulse generator and a lead having a plurality of electrodes. The method includes receiving a first response for each of a plurality of first monopolar stimulations performed using a subset of one or more of the electrodes of the lead as a cathode for each of the first monopolar stimulations; selecting a first subset of one or more of the electrodes based on the first responses; receiving a second response for each of a plurality of second monopolar stimulations performed using a subset of one or more of the electrodes of the lead as an anode for each of the second monopolar stimulations; selecting a second subset of one or more of the electrodes based on the second responses; selecting a programming subset of one or more of the electrodes based, at least in part, on the responses associated with the first subset and second subset; receiving a third response for each of a plurality of third monopolar stimulations performed using the programming subset with each of the third monopolar stimulation having a different stimulation amplitude; selecting a programming stimulation amplitude based on the third responses; receiving direction to program the implantable pulse generator with the programming subset of one or more of the electrodes and the programming stimulation amplitude; and initiating a signal that provides the implantable pulse generator of the electrical stimulation system with the programming subset of one or more of the electrodes and the programming stimulation amplitude for generating electrical stimulation for the patient through the electrodes of the lead.

A further aspect is non-transitory computer-readable medium having computer executable instructions stored thereon that, when executed by a processor, cause the processor to perform the method described above.

In at least some aspects, receiving a first response includes receiving a first quantitative or qualitative indication of at least one therapeutic effect and receiving a second response includes receiving a second quantitative or qualitative indication of at least one therapeutic effect. In at least some aspects, receiving a first response includes receiving a first quantitative or qualitative indication of at least one therapeutic effect, at least one side-effect, or any combination thereof and receiving a second response includes receiving a second quantitative or qualitative indication of at least one therapeutic effect, at least one side-effect, or any combination thereof. In at least some aspects, selecting the set of program stimulation parameters includes selecting the set of program stimulation parameters based on the first and second quantitative or qualitative indications.

In at least some aspects, the processor is further configured to, or the method further includes steps to, receive a third response for each of a plurality of cathodic/anodic stimulations performed using a subset of one or more of the electrodes of the lead as an anode and one or more of the electrodes of the lead as a cathode for each of the cathodic/anodic stimulations; and select a third subset of one or more of the electrodes based on the third responses; wherein selecting the programming subset of one or more of the electrodes includes selecting the programming subset of one or more of the electrodes based, at least in part, on the first, second, and third responses associated with the first subset, second subset, and third subset.

In at least some aspects, receiving a first response including receiving the first response from a clinician or patient. In at least some aspects, receiving a first response including receiving the first response from a sensor.

Another aspect is a system for programming electrical stimulation of a patient using an implantable electrical stimulation system including an implantable pulse generator and a lead having a plurality of electrodes. The system includes a processor configured to receive a first response for each of a plurality of first stimulations performed using a subset of one or more of the electrodes of the lead for each of the first stimulations, wherein the first stimulations are configured to preferentially stimulate a first type of neural element; select a first subset of one or more of the electrodes based, at least in part, on the first responses; receive a second response for each of a plurality of second stimulations performed using a subset of one or more of the electrodes for each of the second stimulations, wherein the second stimulations are configured to preferentially stimulate a second type of neural element which is different from the first type of neural element; select a second subset of one or more of the electrodes based, at least in part, on the second responses; select a programming subset of one or more of the electrodes based on the responses associated with the first subset and second subset; receive direction to program the implantable pulse generator with the programming subset of one or more of the electrodes and the programming stimulation amplitude; and initiate a signal that provides the implantable pulse generator of the electrical stimulation system with the programming subset of one or more of the electrodes and the programming stimulation amplitude for generating electrical stimulation for the patient through the electrodes of the lead.

Yet another aspect is a method for programming electrical stimulation of a patient using an implantable electrical stimulation system including an implantable pulse generator and a lead having a plurality of electrodes. The method includes receiving a first response for each of a plurality of first stimulations performed using a subset of one or more of the electrodes of the lead for each of the first stimulations, wherein the first stimulations are configured to preferentially stimulate a first type of neural element; selecting a first subset of one or more of the electrodes based, at least in part, on the first responses; receiving a second response for each of a plurality of second stimulations performed using a subset of one or more of the electrodes for each of the second stimulations, wherein the second stimulations are configured to preferentially stimulate a second type of neural element which is different from the first type of neural element; selecting a second subset of one or more of the electrodes based, at least in part, on the second responses; selecting a programming subset of one or more of the electrodes based on the responses associated with the first subset and second subset; receiving direction to program the implantable pulse generator with the programming subset of one or more of the electrodes and the programming stimulation amplitude; and initiating a signal that provides the implantable pulse generator of the electrical stimulation system with the programming subset of one or more of the electrodes and the programming stimulation amplitude for generating electrical stimulation for the patient through the electrodes of the lead.

A further aspect is non-transitory computer-readable medium having computer executable instructions stored thereon that, when executed by a processor, cause the processor to perform the method described above.

In at least some aspects, receiving a first response includes receiving a first quantitative or qualitative indication of at least one therapeutic effect and receiving a second response includes receiving a second quantitative or qualitative indication of at least one therapeutic effect. In at least some aspects, receiving a first response includes receiving a first quantitative or qualitative indication of at least one therapeutic effect, at least one side-effect, or any combination thereof and receiving a second response includes receiving a second quantitative or qualitative indication of at least one therapeutic effect, at least one side-effect, or any combination thereof. In at least some aspects, selecting the set of program stimulation parameters includes selecting the set of program stimulation parameters based on the first and second quantitative or qualitative indications.

In at least some aspects, the processor is further configured to, or the method further includes steps to, receive a third response for each of a plurality of third stimulations performed using a subset of one or more of the electrodes for each of the third stimulations, wherein the third stimulations are configured to preferentially stimulate a third type of neural element which is different from the first and second types of neural element; and select a third subset of one or more of the electrodes based, at least in part, on the third responses; wherein selecting the programming subset of one or more of the electrodes includes selecting the programming subset of one or more of the electrodes based, at least in part, on the first, second, and third responses associated with the first subset, second subset, and third subset.

In at least some aspects, receiving a first response including receiving the first response from a clinician or patient. In at least some aspects, receiving a first response including receiving the first response from a sensor.

Another aspect is a system for programming electrical stimulation of a patient using an implantable electrical stimulation system including an implantable pulse generator and a lead having a plurality of electrodes. The system includes a processor configured to receive a first response for each of a plurality of first monopolar stimulations performed using at least one of the electrodes of the lead as a cathode, each of the first monopolar stimulations having a set of first stimulation parameters associated with the first stimulation; receive a second response for each of a plurality of second monopolar stimulations performed using at least one of the electrodes of the lead as an anode, each of the second monopolar stimulations having a set of second stimulation parameters associated with the second stimulation; select, from the sets of first stimulation parameters and sets of second stimulation parameters, a set of program stimulation parameters for a first stimulation program based on the first and second responses; receive direction to program the implantable pulse generator with the set of program stimulation parameters; and initiate a signal that provides the implantable pulse generator of the electrical stimulation system with the set of program stimulation parameters for generating electrical stimulation for the patient through the electrodes of the lead.

Yet another aspect is a method for programming electrical stimulation of a patient using an implantable electrical stimulation system including an implantable pulse generator and a lead having a plurality of electrodes. The method includes receiving a first response for each of a plurality of first monopolar stimulations performed using at least one of the electrodes of the lead as a cathode, each of the first monopolar stimulations having a set of first stimulation parameters associated with the first stimulation; receiving a second response for each of a plurality of second monopolar stimulations performed using at least one of the electrodes of the lead as an anode, each of the second monopolar stimulations having a set of second stimulation parameters associated with the second stimulation; selecting, from the sets of first stimulation parameters and sets of second stimulation parameters, a set of program stimulation parameters for a first stimulation program based on the first and second responses; receiving direction to program the implantable pulse generator with the set of program stimulation parameters; and initiating a signal that provides the implantable pulse generator of the electrical stimulation system with the set of program stimulation parameters for generating electrical stimulation for the patient through the electrodes of the lead.

A further aspect is non-transitory computer-readable medium having computer executable instructions stored thereon that, when executed by a processor, cause the processor to perform the method described above.

In at least some aspects, receiving a first response includes receiving a first quantitative or qualitative indication of at least one therapeutic effect and receiving a second response includes receiving a second quantitative or qualitative indication of at least one therapeutic effect. In at least some aspects, receiving a first response includes receiving a first quantitative or qualitative indication of at least one therapeutic effect, at least one side-effect, or any combination thereof and receiving a second response includes receiving a second quantitative or qualitative indication of at least one therapeutic effect, at least one side-effect, or any combination thereof. In at least some aspects, selecting the set of program stimulation parameters includes selecting the set of program stimulation parameters based on the first and second quantitative or qualitative indications.

In at least some aspects, receiving a first response including receiving the first response from a clinician or patient. In at least some aspects, receiving a first response including receiving the first response from a sensor.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

Figure 1:
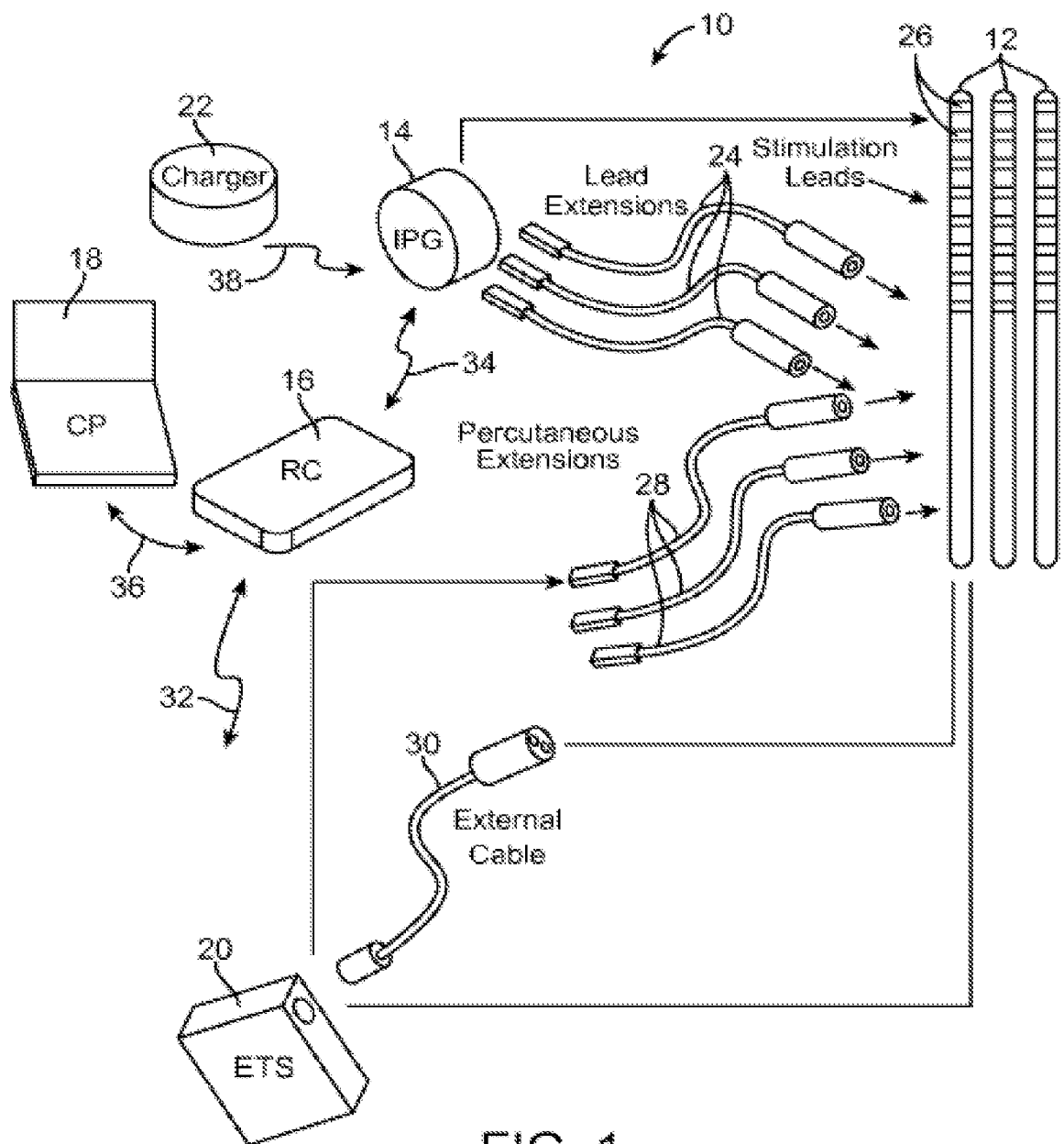
FIG. 1 is a schematic view of one embodiment of an electrical stimulation system.

The present disclosure is directed to the area of implantable electrical stimulation systems and methods of making and using the systems. The present disclosure is also directed to electrical stimulation systems with multiple modes, such as anodic or cathodic stimulation modes, and methods of making and using.

Suitable implantable electrical stimulation systems include, but are not limited to, a least one lead with one or more electrodes disposed on a distal end of the lead and one or more terminals disposed on one or more proximal ends of the lead. Leads include, for example, percutaneous leads, paddle leads, cuff leads, or any other arrangement of electrodes on a lead. Examples of electrical stimulation systems with leads are found in, for example, U.S. Pat. Nos. 6,181,969; 6,516,227; 6,609,029; 6,609,032; 6,741,892; 7,244,150; 7,450,997; 7,672,734; 7,761,165; 7,783,359; 7,792,590; 7,809,446; 7,949,395; 7,974,706; 8,175,710; 8,224,450; 8,271,094; 8,295,944; 8,364,278; 8,391,985; and 8,688,235; and U.S. Patent Applications Publication Nos. 2007/0150036; 2009/0187222; 2009/0276021; 2010/0076535; 2010/0268298; 2011/0005069; 2011/0004267; 2011/0078900; 2011/0130817; 2011/0130818; 2011/0238129; 2011/0313500; 2012/0016378; 2012/0046710; 2012/0071949; 2012/0165911; 2012/0197375; 2012/0203316; 2012/0203320; 2012/0203321; 2012/0316615; 2013/0105071; and 2013/0197602, all of which are incorporated by reference. In the discussion below, a percutaneous lead will be exemplified, but it will be understood that the methods and systems described herein are also applicable to paddle leads and other leads.

A percutaneous lead for electrical stimulation (for example, deep brain or spinal cord stimulation) includes stimulation electrodes that can be ring electrodes, segmented electrodes that extend only partially around the circumference of the lead, or any other type of electrode, or any combination thereof. The segmented electrodes can be provided in sets of electrodes, with each set having electrodes circumferentially distributed about the lead at a particular longitudinal position. For illustrative purposes, the leads are described herein relative to use for deep brain stimulation, but it will be understood that any of the leads can be used for applications other than deep brain stimulation, including spinal cord stimulation, peripheral nerve stimulation, or stimulation of other nerves, muscles, and tissues. In particular, stimulation may stimulate specific targets. Examples of such targets include, but are not limited to, the subthalamic nucleus (STN), internal segment of the globus pallidus (GPi), external segment of the globus pallidus (GPe), and the like. In at least some embodiments, an anatomical structure is defined by its physical structure and a physiological target is defined by its functional attributes. In at least one of the various embodiments, the lead may be positioned at least partially within the target, but in other embodiments, the lead may be near, but not inside, the target.

Turning to FIG. 1, one embodiment of an electrical stimulation system 10 includes one or more stimulation leads 12 and an implantable pulse generator (IPG) 14. The system 10 can also include one or more of an external remote control (RC) 16, a clinician's programmer (CP) 18, an external trial stimulator (ETS) 20, or an external charger 22.

The IPG 14 is physically connected, optionally via one or more lead extensions 24, to the stimulation lead(s) 12. Each lead carries multiple electrodes 26 arranged in an array. The IPG 14 includes pulse generation circuitry that delivers electrical stimulation energy in the form of, for example, a pulsed electrical waveform (i.e., a temporal series of electrical pulses) to the electrode array 26 in accordance with a set of stimulation parameters. The IPG 14 can be implanted into a patient's body, for example, below the patient's clavicle area or within the patient's buttocks or abdominal cavity. The IPG 14 can have eight stimulation channels which may be independently programmable to control the magnitude of the current stimulus from each channel. In at least some embodiments, the IPG 14 can have more or fewer than eight stimulation channels (for example, 4-, 6-, 16-, 32-, or more stimulation channels). The IPG 14 can have one, two, three, four, or more connector ports, for receiving the terminals of the leads.

The ETS 20 may also be physically connected, optionally via the percutaneous lead extensions 28 and external cable 30, to the stimulation leads 12. The ETS 20, which may have similar pulse generation circuitry as the IPG 14, also delivers electrical stimulation energy in the form of, for example, a pulsed electrical waveform to the electrode array 26 in accordance with a set of stimulation parameters. One difference between the ETS 20 and the IPG 14 is that the ETS 20 is often a non-implantable device that is used on a trial basis after the neurostimulation leads 12 have been implanted and prior to implantation of the IPG 14, to test the responsiveness of the stimulation that is to be provided. Any functions described herein with respect to the IPG 14 can likewise be performed with respect to the ETS 20. In at least some embodiments, the ETS can be connected to an external electrode (for example, a patch, or plate) or to the surgical equipment (for example, frame, cannula, etc.) to serve as a return electrode for the purposes of, for example, monopolar stimulation.

The RC 16 may be used to telemetrically communicate with or control the IPG 14 or ETS 20 via a uni- or bi-directional wireless communications link 32. Once the IPG 14 and neurostimulation leads 12 are implanted, the RC 16 may be used to telemetrically communicate with or control the IPG 14 via a uni- or bi-directional communications link 34. Such communication or control allows the IPG 14 to be turned on or off and to be programmed with different stimulation parameter sets. The IPG 14 may also be operated to modify the programmed stimulation parameters to actively control the characteristics of the electrical stimulation energy output by the IPG 14. The CP 18 allows a user, such as a clinician, the ability to program stimulation parameters for the IPG 14 and ETS 20 in the operating room and in follow-up sessions.

The CP 18 may perform this function by indirectly communicating with the IPG 14 or ETS 20, through the RC 16, via a wireless communications link 36. Alternatively, the CP 18 may directly communicate with the IPG 14 or ETS 20 via a wireless communications link (not shown). The stimulation parameters provided by the CP 18 are also used to program the RC 16, so that the stimulation parameters can be subsequently modified by operation of the RC 16 in a stand-alone mode (i.e., without the assistance of the CP 18).

For purposes of brevity, the details of the RC 16, CP 18, ETS 20, and external charger 22 will not be further described herein. Details of exemplary embodiments of these devices are disclosed in U.S. Pat. No. 6,895,280, which is expressly incorporated herein by reference. Other examples of electrical stimulation systems can be found at U.S. Pat. Nos. 6,181,969; 6,516,227; 6,609,029; 6,609,032; 6,741,892; 7,949,395; 7,244,150; 7,672,734; and 7,761,165; 7,974,706; 8,175,710; 8,224,450; and 8,364,278; and U.S. Patent Application Publication No. 2007/0150036, as well as the other references cited above, all of which are incorporated by reference.

Figure 2:
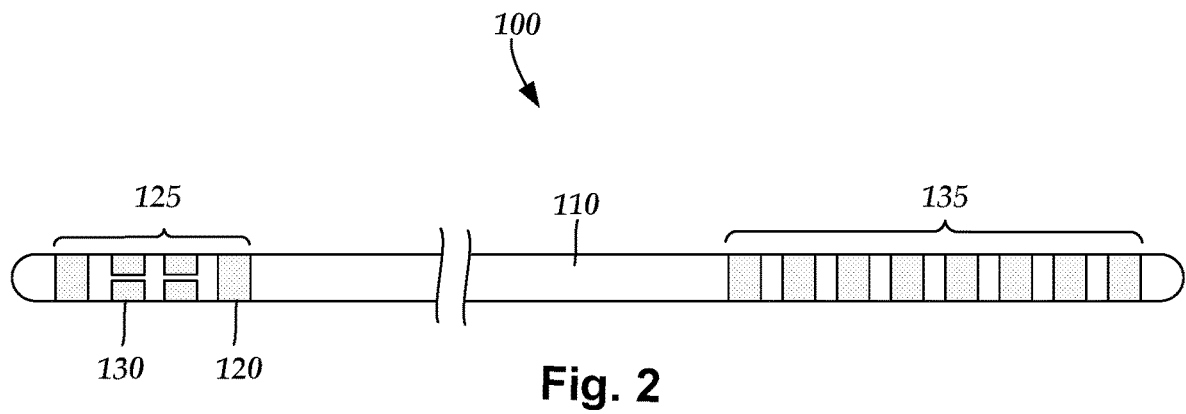
FIG. 2 is a schematic side view of one embodiment of an electrical stimulation lead.

FIG. 2 illustrates one embodiment of a lead 100 with electrodes 125 disposed at least partially about a circumference of the lead 100 along a distal end portion of the lead 100 and terminals 135 disposed along a proximal end portion of the lead 100. The lead 100 can be implanted near or within the desired portion of the body to be stimulated such as, for example, the brain, spinal cord, or other body organs or tissues. In one example of operation for deep brain stimulation, access to the desired position in the brain can be accomplished by drilling a hole in the patient's skull or cranium with a cranial drill (commonly referred to as a burr), and coagulating and incising the dura mater, or brain covering. The lead 100 can be inserted into the cranium and brain tissue with the assistance of a stylet (not shown). The lead 100 can be guided to the target location within the brain using, for example, a stereotactic frame and a microdrive motor system. In at least some embodiments, the microdrive motor system can be fully or partially automatic. The microdrive motor system may be configured to perform one or more the following actions (alone or in combination): insert the lead 100, advance the lead 100, retract the lead 100, or rotate the lead 100.

In at least some embodiments, measurement devices coupled to the muscles or other tissues stimulated by the target neurons, or a unit responsive to the patient or clinician, can be coupled to the IPG 14 or microdrive motor system. The measurement device, user, or clinician can indicate a response by the target muscles or other tissues to the stimulation or recording electrode(s) to further identify the target neurons and facilitate positioning of the stimulation electrode(s). For example, if the target neurons are directed to a muscle experiencing tremors, a measurement device can be used to observe the muscle and indicate changes in, for example, tremor frequency or amplitude in response to stimulation of neurons. Alternatively, the patient or clinician can observe the muscle and provide feedback.

The lead 100 for deep brain stimulation can include stimulation electrodes, recording electrodes, or both. In at least some embodiments, the lead 100 is rotatable so that the stimulation electrodes can be aligned with the target neurons after the neurons have been located using the recording electrodes.

Stimulation electrodes may be disposed on the circumference of the lead 100 to stimulate the target neurons. Stimulation electrodes may be ring-shaped so that current projects from each electrode equally in every direction from the position of the electrode along a length of the lead 100. In the embodiment of FIG. 2, two of the electrodes 125 are ring electrodes 120. Ring electrodes typically do not enable stimulus current to be directed from only a limited angular range around a lead. Segmented electrodes 130, however, can be used to direct stimulus current to a selected angular range around a lead. When segmented electrodes are used in conjunction with an implantable pulse generator that delivers constant current stimulus, and preferably includes multiple current sources, current steering can be achieved to more precisely deliver the stimulus to a position around an axis of a lead (i.e., radial positioning around the axis of a lead). To achieve current steering, segmented electrodes can be utilized in addition to, or as an alternative to, ring electrodes.

The lead 100 includes a lead body 110, terminals 135, one or more ring electrodes 120, and one or more sets of segmented electrodes 130 (or any other combination of electrodes). The lead body 110 can be formed of a biocompatible, non-conducting material such as, for example, a polymeric material. Suitable polymeric materials include, but are not limited to, silicone, polyurethane, polyurea, polyurethane-urea, polyethylene, or the like. Once implanted in the body, the lead 100 may be in contact with body tissue for extended periods of time. In at least some embodiments, the lead 100 has a cross-sectional diameter of no more than 1.5 mm and may be in the range of 0.5 to 1.5 mm. In at least some embodiments, the lead 100 has a length of at least 10 cm and the length of the lead 100 may be in the range of 10 to 70 cm.

The electrodes 125 can be made using a metal, alloy, conductive oxide, or any other suitable conductive biocompatible material. Examples of suitable materials include, but are not limited to, platinum, platinum iridium alloy, iridium, titanium, tungsten, palladium, palladium rhodium, or the like. Preferably, the electrodes 125 are made of a material that is biocompatible and does not substantially corrode under expected operating conditions in the operating environment for the expected duration of use.

Each of the electrodes 125 can either be used or unused (OFF). When an electrode is used, the electrode can be used as an anode or cathode and carry anodic or cathodic current. In some instances, an electrode might be an anode for a period of time and a cathode for a period of time.

Deep brain stimulation leads may include one or more sets of segmented electrodes. Segmented electrodes may provide for superior current steering than ring electrodes because target structures in deep brain stimulation are not typically symmetric about the axis of the distal electrode array. Instead, a target may be located on one side of a plane running through the axis of the lead. Through the use of a radially segmented electrode array ("RSEA"), current steering can be performed not only along a length of the lead but also around a circumference of the lead. This provides precise three-dimensional targeting and delivery of the current stimulus to neural target tissue, while potentially avoiding stimulation of other tissue. Examples of leads with segmented electrodes include U.S. Pat. Nos. 8,473,061; 8,571,665; and 8,792,993; U.S. Patent Application Publications Nos. 2010/0268298; 2011/0005069; 2011/0130803; 2011/0130816; 2011/0130817; 2011/0130818; 2011/0078900; 2011/0238129; 2012/0016378; 2012/0046710; 2012/0071949; 2012/0165911; 2012/197375; 2012/0203316; 2012/0203320; 2012/0203321; 2013/0197424; 2013/0197602; 2014/0039587; 2014/0353001; 2014/0358208; 2014/0358209; 2014/0358210; 2015/0045864; 2015/0066120; 2015/0018915; 2015/0051681; U.S. patent application Ser. Nos. 14/557,211 and 14/286,797; and U.S. Provisional Patent Application Ser. No. 62/113,291, all of which are incorporated herein by reference.

Figure 3:
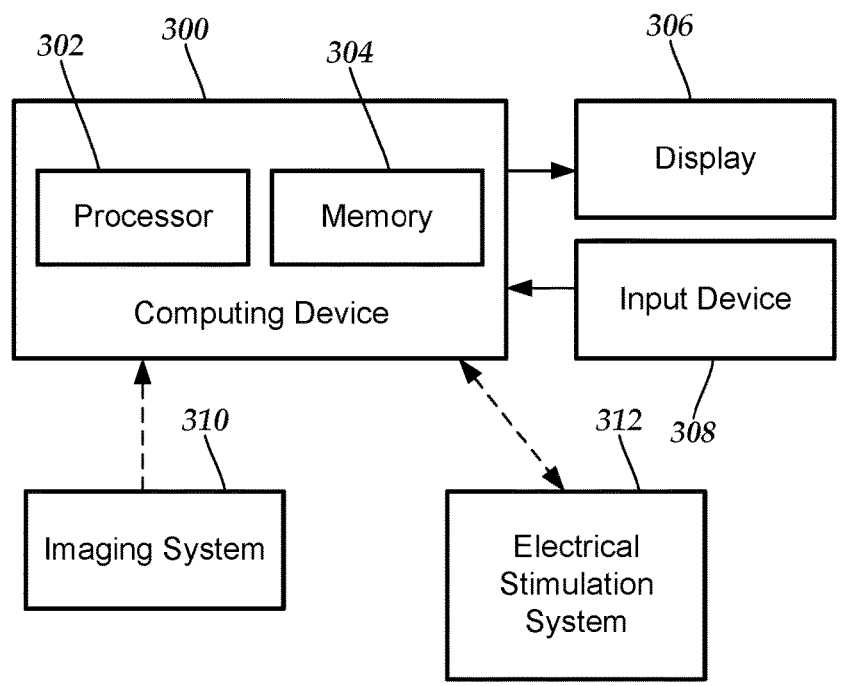
FIG. 3 is a schematic block diagram of one embodiment of a system for determining stimulation parameters.

FIG. 3 illustrates one embodiment of a system for practicing the invention. The system can include a computing device 300 or any other similar device that includes a processor 302 and a memory 304, a display 306, an input device 308, and, optionally, an electrical stimulation system 312. The system 300 may also optionally include one or more imaging systems 310.

The computing device 300 can be a computer, tablet, mobile device, or any other suitable device for processing information. The computing device 300 can be local to the user or can include components that are non-local to the computer including one or both of the processor 302 or memory 304 (or portions thereof). For example, in at least some embodiments, the user may operate a terminal that is connected to a non-local computing device. In other embodiments, the memory can be non-local to the user.

The computing device 300 can utilize any suitable processor 302 and the term "a processor" can include one or more hardware processors within the computing device or other components of the system or may be local to the user or non-local to the user or other components of the computing device. The processor 302 is configured to execute instructions provided to the processor 302, as described below.

Any suitable memory 304 can be used for the computing device 302. The memory 304 illustrates a type of computer-readable media, namely computer-readable storage media. Computer-readable storage media may include, but is not limited to, nonvolatile, non-transitory, removable, and non-removable media implemented in any method or technology for storage of information, such as computer readable instructions, data structures, program modules, or other data. Examples of computer-readable storage media include RAM, ROM, EEPROM, flash memory, or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a computing device.

Communication methods provide another type of computer readable media; namely communication media. Communication media typically embodies computer-readable instructions, data structures, program modules, or other data in a modulated data signal such as a carrier wave, data signal, or other transport mechanism and include any information delivery media. The terms "modulated data signal," and "carrier-wave signal" includes a signal that has one or more of its characteristics set or changed in such a manner as to encode information, instructions, data, and the like, in the signal. By way of example, communication media includes wired media such as twisted pair, coaxial cable, fiber optics, wave guides, and other wired media and wireless media such as acoustic, RF, infrared, and other wireless media.

The display 306 can be any suitable display device, such as a monitor, screen, display, or the like, and can include a printer. The input device 308 can be, for example, a keyboard, mouse, touch screen, track ball, joystick, voice recognition system, or any combination thereof, or the like.

One or more imaging systems 310 can be used including, but not limited to, MRI, computed tomography (CT), ultrasound, or other imaging systems. The imaging system 310 may communicate through a wired or wireless connection with the computing device 300 or, alternatively or additionally, a user can provide images from the imaging system 310 using a computer-readable medium or by some other mechanism.

The electrical stimulation system 312 can include, for example, any of the components illustrated in FIG. 1. The electrical stimulation system 312 may communicate with the computing device 300 through a wired or wireless connection or, alternatively or additionally, a user can provide information between the electrical stimulation system 312 and the computing device 300 using a computer-readable medium or by some other mechanism. In at least some embodiments, the computing device 300 may include part of the electrical stimulation system, such as, for example, the IPG 14, CP 18, RC 16, ETS 20, or any combination thereof.

The methods and systems described herein may be embodied in many different forms and should not be construed as limited to the embodiments set forth herein. Accordingly, the methods and systems described herein may take the form of an entirely hardware embodiment, an entirely software embodiment or an embodiment combining software and hardware aspects. Systems referenced herein typically include memory and typically include methods for communication with other devices including mobile devices. Methods of communication can include both wired and wireless (for example, RF, optical, or infrared) communications methods and such methods provide another type of computer readable media; namely communication media. Wired communication can include communication over a twisted pair, coaxial cable, fiber optics, wave guides, or the like, or any combination thereof. Wireless communication can include RF, infrared, acoustic, near field communication, Bluetooth™, or the like, or any combination thereof.

Stimulation therapy can be used to treat a number of diseases, disorders, and conditions including, but not limited to, pain, Parkinson's Disease, Alzheimer's Disease, essential tremor, epilepsy, dystonia, depression, obsessive-compulsive disorder, addiction, Tourette's syndrome, eating disorders (such as anorexia, bulimia, or obesity), other neurological diseases and disorders, or the like. To provide a stimulation therapy, the stimulation parameters for the therapy may be determined during a programming session. In at least some embodiments, in a programming session a clinician will vary stimulation parameters and measure the resulting stimulation effects or side effects. For example, a score can be associated with any stimulation effect or side effect associated with the set of stimulation parameters. For example, in a patient afflicted with Parkinson's Disease, the score may be based on any suitable rating scale (for example, the Unified Parkinson's Disease Rating Scale (UPDRS)).

In many electrical stimulation systems, cathodic stimulation is used to stimulate patient tissue. Cathodic stimulation is known to preferentially activate neural fibers near the cathode or cathodes. In contrast to cathodic stimulation, anodic stimulation (e.g., stimulation near an anode) can activate different neural elements, such as neural cells. Moreover, the threshold for stimulation of many neural elements is different for anodic and cathodic stimulation. As an example, U.S. Pat. No. 6,560,490, incorporated herein by reference in its entirety, demonstrates in FIGS. 1 and 2 that cathodic stimulation activates nerve fibers at much lower stimulation amplitudes than neuronal cells. In contrast, anodic stimulation activates neuronal cells at lower stimulation amplitudes than nerve fibers.

Because anodic stimulation activates neural tissue differently from cathodic stimulation, it may be difficult to know which type of stimulation may best produce desired therapeutic effects or best avoid undesirable side-effects. Systems can be programmed with methods to facilitate selection of beneficial programming using cathodic or anodic stimulation or any combination thereof. Embodiment of such systems can include, for example, the system illustrated in FIG. 3, the CP 18 or RC 16 of FIG. 1, or any other suitable system or device.

In many instances, for monopolar cathodic stimulation, the anode of the electrical stimulation system is located on the case of the implantable pulse generator or at another site relatively distant from the cathode or cathodes on the lead. Monopolar cathodic stimulation may also include instances where the anode is distributed over a large number of (for example, at least four, five, six, seven, or more) electrodes on the lead or where the anode is positioned on the lead at a substantial distance away from the cathode (for example, the anode is near the proximal end of the array of electrodes and the cathode is near the proximal end of the electrodes.) Similarly, monopolar anodic stimulation may include instances where the cathode of the electrical stimulation system is located on the case of the implantable pulse generator or at another site relatively distant from the anode or anodes on the lead or instances where the cathode is distributed over a large number of (for example, at least four, five, six, seven, or more) electrodes on the lead or where the cathode is positioned on the lead at a substantial distance away from the anode (for example, the anode is near the proximal end of the array of electrodes and the cathode is near the proximal end of the electrodes.) Another method for identifying the anodic or cathodic nature of stimulation can be found in U.S. Pat. No. 8,190,250, incorporated herein by reference in its entirety, which observes the angle of an electric field at particular points with respect to the lead.

Figure 4A:
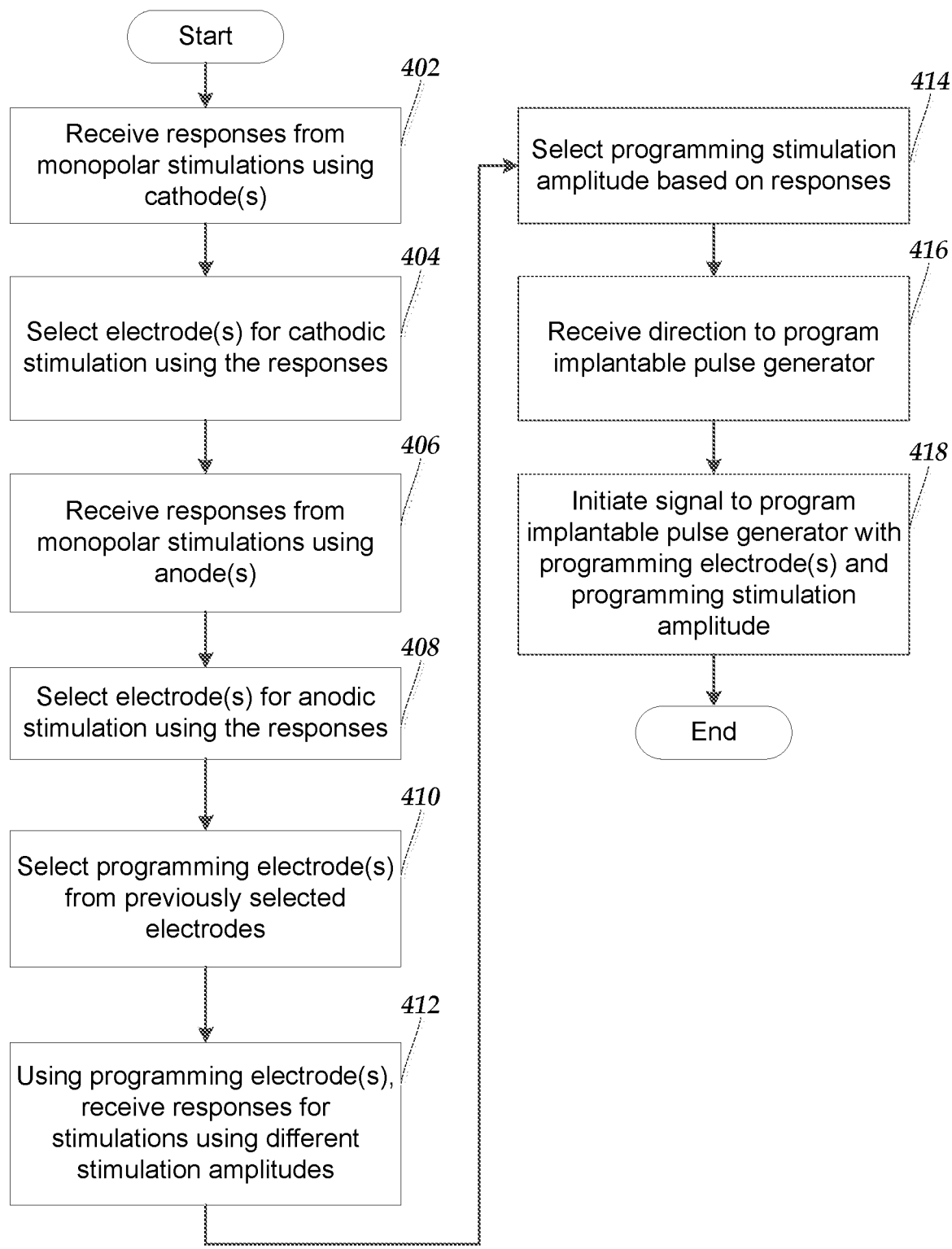
FIG. 4A is a flowchart of one embodiment of a method for programming electrical stimulation of a patient.

FIG. 4A illustrates one method of selecting stimulation parameters for an electrical stimulation system. In step 402, responses are received for multiple monopolar stimulations performed using a subset of one or more electrodes of a lead as a cathode for each of the monopolar stimulations. In at least some embodiments, other stimulation parameters, such as stimulation amplitude, pulse width, and pulse duration, may be the same for all of the stimulations. In other embodiments, other stimulation parameters, such as stimulation amplitude, pulse width, and pulse duration, may be different for at least some of the stimulations. For example, if a particular stimulation is painful or generates unacceptable side effects, the stimulation amplitude may be reduced and stimulation using the same electrode(s) may be performed with the reduced stimulation amplitude.

The responses to stimulation can be any quantitative or qualitative assessment of the stimulation itself, one or more therapeutic effects, or one or more side-effects, or any combination thereof. For example, the response may include a rating of the stimulation itself on a scale of numbers or qualitative scale (e.g., ineffective, good, poor, unacceptable). As another example, the response may include a rating of one or more beneficial therapeutic effects or side-effects on a scale of numbers or qualitative scale. If more than one effect is rated, the rating may be an overall rating or there may be multiple ratings for each effect. The response may be from the programmer or other clinician directing the stimulations or from the patient or from one or more sensors or other device that monitor the patient or from any combination of these sources.

In step 404, the responses are evaluated and, based on the responses, one or more electrodes are selected for cathodic stimulation. Any suitable criteria can be used. For example, the electrode(s) which provided the most beneficial therapeutic effect may be selected. As another example, the electrode(s) that provided the most beneficial therapeutic effect with no side-effects (or with side-effects below a selected threshold) may be selected.

In step 406, responses are received for multiple monopolar stimulations performed using a subset of one or more electrodes of a lead as an anode for each of the monopolar stimulations. The responses may be assessed using the same or a different assessment as those in step 402. In some embodiments, the stimulation parameters used for the stimulations of step 402 are also used in step 406. In other embodiments, different stimulation parameters (for example, a different stimulation amplitude, pulse width, or pulse duration, or any combination thereof) may be used due to the differences in neural activation between anodic and cathodic stimulation.

The monopolar stimulations in steps 402 and 406 may be performed in any order and may be intermingled. For example, the monopolar stimulations in step 402 may be performed first followed by the monopolar stimulations in step 406. In another example, the monopolar stimulations in step 406 may be performed first followed by the monopolar stimulations in step 402. In yet another example, one or more monopolar stimulations in step 402 may be performed followed by one or more monopolar stimulations in step 406 followed by further monopolar stimulation(s) in step 402, and so on. For example, cathodic stimulation using a particular subset of one or more electrodes can be performed in step 402 followed by anodic stimulation using the same subset of one or more electrodes in step 406 and this pattern can be repeated for multiple different subsets of one or more electrodes.

In step 408, these responses are evaluated and, based on the responses, one or more electrodes are selected for anodic stimulation. The criteria used for selecting the one or more electrodes may be the same or different as those in step 404.

Figure 4B:
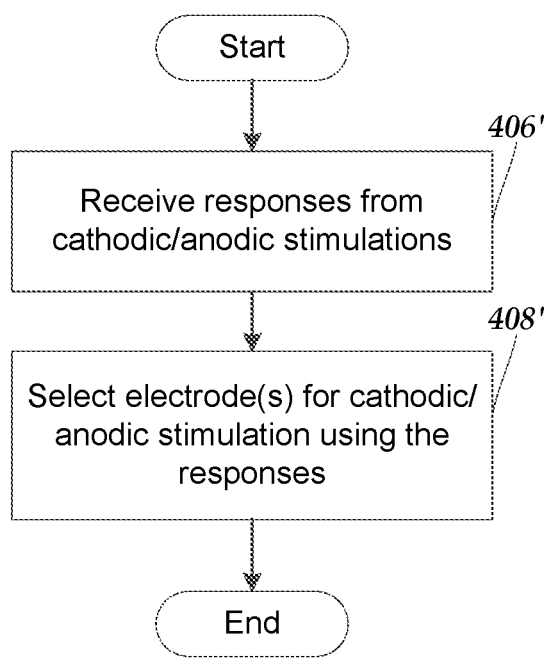
FIG. 4B is a flowchart of additional steps that can be added to the flowchart of FIG. 4A.

In some embodiments, the steps 406' and 408' of FIG. 4B can be added one or more times after step 408. In step 406', responses are received for multiple bipolar or multipolar stimulations utilizing both anodic and cathodic stimulation (i.e., cathodic/anodic stimulation). In step 408', these responses are evaluated and, based on the responses, one or more electrodes are selected for cathodic/anodic stimulation. In such instances, multiple electrodes (one or more anodes and one or more cathodes) will be used to provide the stimulation. For example, steps 406' and 408' may be performed using a combination of 50% anodic and 50% cathodic stimulation, or 25% anodic and 75% cathodic, or any other combination. Steps 406' and 408' may be performed one, two, three, four, or more times using different relative amounts of anodic and cathodic stimulation. It will be understood that that the relative strengths of anode and cathode on the lead can be different, and this may be accomplished by putting some current of one polarity at the case or housing of the IPG (or other distant location). The sum of the currents for a given polarity must be equal to the sum of the currents for the other polarity.

Returning to FIG. 4A, in step 410, the selected electrode(s) of step 404 or the selected electrode(s) of step 408 (or, optionally, any selected electrode(s) from one or more instances of step 408' of FIG. 4B) is selected as programming electrode(s). Any criteria can be used for selecting between the electrode(s) identified in steps 404 and 408 (and, optionally, any selected electrode(s) from one or more instances of step 408' of FIG. 4B). For example, the electrode(s) which provided the most beneficial therapeutic effect may be selected. As another example, the electrode(s) that provided the most beneficial therapeutic effect with no side-effects (or with side-effects below a selected threshold) may be selected.

In step 412, responses are received for stimulations performed using the programming electrode(s) selected in step 410 at a series of different stimulation amplitudes.

In step 414, a programming stimulation amplitude is selected based on the responses received in step 412. Any criteria can be used for selecting the programming stimulation amplitude. For example, the stimulation amplitude that provided the most beneficial therapeutic effect with no side-effects (or with side-effects below a selected threshold) may be selected.

In some embodiments, steps 412 and 414 may be repeated for other stimulation parameters in place of stimulation amplitude. For example, in some embodiments, steps 412 and 414 may be repeated for pulse width instead of stimulation amplitude. In some embodiments, steps 412 and 414 may be repeated for pulse duration or pulse rate instead of stimulation amplitude. Any subset of additional stimulation parameters may be titrated and selected using the procedure of steps 412 and 414; typically, with previously selected stimulation parameters being held at their selected value.

In step 416, the system is directed to program the implantable pulse generator. In at least some embodiments, this direction may be automatic upon selecting the electrodes and stimulation amplitude (and, optionally, other stimulation parameter(s)). In some embodiments, the direction is made by a clinician, programmer, or other user.

In step 418, a signal is initiated by the system to program the implantable pulse generator with stimulation parameters including the programming electrode(s) and programming stimulation amplitude (and, optionally, other stimulation parameter(s)). The implantable pulse generator can then use this programming to stimulate the patient through the attached lead and electrodes.

Figure 5B:
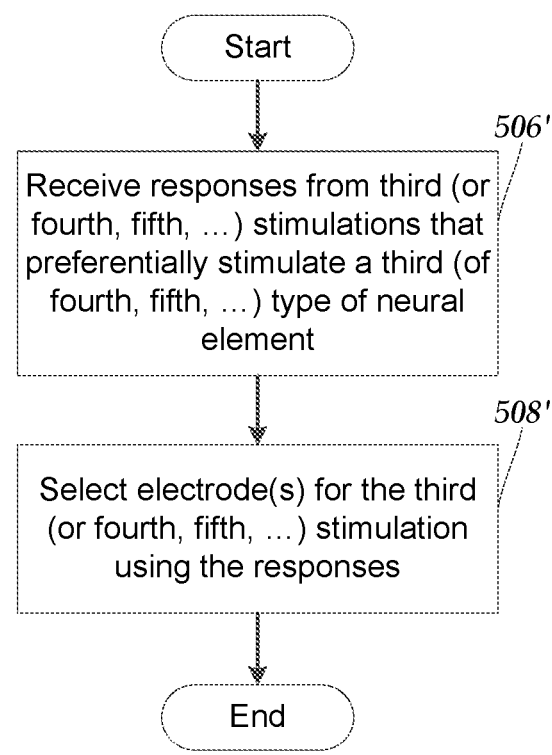
FIG. 5B is a flowchart of additional steps that can be added to the flowchart of FIG. 5A.
Figure 5A:
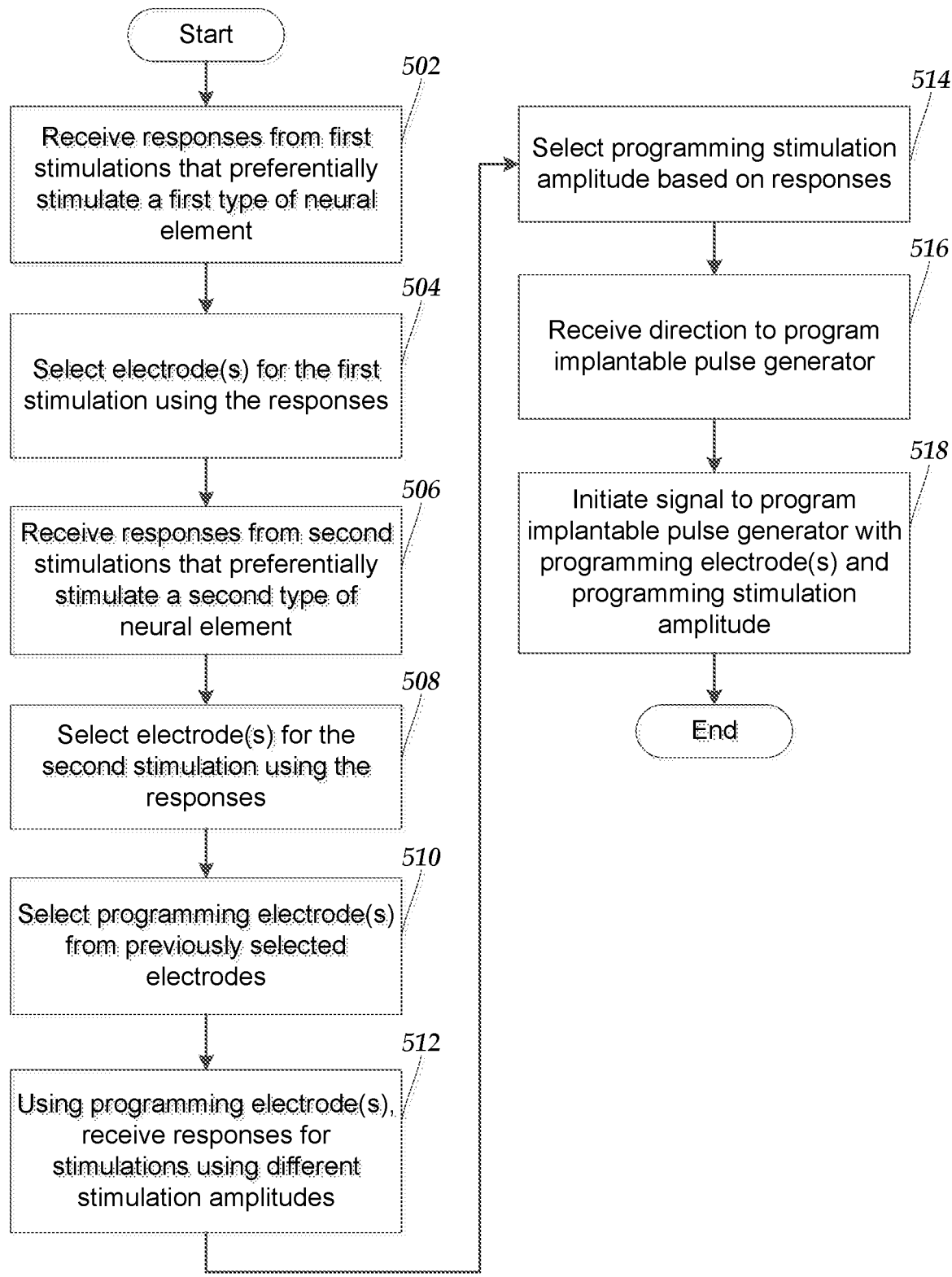
FIG. 5A is a flowchart of another embodiment of a method for programming electrical stimulation of a patient.

FIG. 5A illustrates one method of selecting stimulation parameters for an electrical stimulation system. In step 502, responses are received for multiple first stimulations performed using different subsets of one or more electrodes of a lead. The first stimulations are selected to preferentially stimulate a first type of neural element. Examples types of neural elements include fibers, cells, neuron terminals, synapses, or neurons with different biophysical properties (such as specific ion channel properties), or the like. Other types may be more specific including, for example, large fibers small fibers, specific types of cells, and the like. The type of neural element may be based on the trajectory of the neural element relative to the lead. For example, one type may be fibers aligned parallel to the lead and another type may be fibers aligned perpendicular to the lead. Such trajectories may be defined by ranges of angles or other geometrical properties.

Preferential stimulation may be based on a variety of factors such as, for example, the geometry of the electrodes (for example, using electrodes near tissue having a relatively high concentration of the particular neural element) or may include stimulation polarity (for example, anodic or cathodic), pulse width, pulse rate, stimulation amplitude, or other electrical factors. As example, cathodic stimulation may activate fibers preferentially with respect to neural cells. Conversely, anodic stimulation may activate neural cells preferentially with respect to fibers.

In at least some embodiments, other stimulation parameters, such as stimulation amplitude, pulse width, and pulse duration, may be the same for all of the stimulations. In other embodiments, other stimulation parameters, such as stimulation amplitude, pulse width, and pulse duration, may be different for at least some of the stimulations. For example, if a particular stimulation is painful or generates unacceptable side effects, the stimulation amplitude may be reduced and stimulation using the same electrode(s) may be performed with the reduced stimulation amplitude.

The responses to stimulation can be any quantitative or qualitative assessment of the stimulation itself, one or more therapeutic effects, or one or more side-effects, or any combination thereof. For example, the response may include a rating of the stimulation itself on a scale of numbers or qualitative scale (e.g., ineffective, good, poor, unacceptable). As another example, the response may include a rating of one or more beneficial therapeutic effects or side-effects on a scale of numbers or qualitative scale. If more than one effect is rated, the rating may be an overall rating or there may be multiple ratings for each effect. The response may be from the programmer or other clinician directing the stimulations or from the patient or from one or more sensors or other device that monitor the patient or from any combination of these sources.

In step 504, the responses are evaluated and, based on the responses, one or more electrodes are selected for preferential stimulation of the first type of neural element. Any suitable criteria can be used. For example, the electrode(s) which provided the most beneficial therapeutic effect may be selected. As another example, the electrode(s) that provided the most beneficial therapeutic effect with no side-effects (or with side-effects below a selected threshold) may be selected.

In step 506, responses are received for multiple second stimulations performed using different subsets of one or more electrodes of a lead. The second stimulations are selected to preferentially stimulate a second type of neural element that is different from the first type of neural element. The responses may be assessed using the same or a different assessment as those in step 502. In some embodiments, the stimulation parameters used for the stimulations of step 502 are also used in step 506. In other embodiments, different stimulation parameters (for example, a different stimulation amplitude, pulse width, or pulse duration, or any combination thereof) may be used due to the differences in neural activation between stimulation of the first and second types of neural elements.

The monopolar stimulations in steps 502 and 506 may be performed in any order and may be intermingled. For example, the stimulations in step 502 may be performed first followed by the stimulations in step 506. In another example, the stimulations in step 506 may be performed first followed by the stimulations in step 502. In yet another example, one or more stimulations in step 502 may be performed followed by one or more stimulations in step 506 followed by further stimulation(s) in step 502, and so on. For example, preferential stimulation of the first type of neural element using a particular subset of one or more electrodes can be performed in step 502 followed by preferential stimulation of the second type of neural element using the same subset of one or more electrodes in step 506 and this pattern can be repeated for multiple different subsets of one or more electrodes.

In step 508, these responses are evaluated and, based on the responses, one or more electrodes are selected for preferential stimulation of the second type of neural element. The criteria used for selecting the one or more electrodes may be the same or different as those in step 504.

In some embodiments, the steps 506' and 508' of FIG. 5B can be performed one, two, three, or more times after step 508. In step 506', responses are received for multiple third (or fourth, fifth, . . . ) stimulations performed using different subsets of one or more electrodes of a lead. The third (or fourth, fifth, . . . ) stimulations are selected to preferentially stimulate a third (or fourth, fifth, . . . ) type of neural element that is different from the first and second (and any other previously selected) types of neural element. The responses may be assessed using the same or different assessment as those in step 502. In step 508', these responses are evaluated and, based on the responses, one or more electrodes are selected for the stimulation of the third (or fourth, fifth, . . . ) type of neural element. The criteria used for selecting the one or more electrodes may be the same or different as those in step 504.

Returning to FIG. 5A, in step 510, the selected electrode(s) of step 504 or the selected electrode(s) of step 508 (or, optionally, any selected electrode(s) from one or more instances of step 508' of FIG. 5B) is selected as programming electrode(s). Any criteria can be used for selecting between the electrode(s) identified in steps 504 and 508 (and, optionally, any selected electrode(s) from one or more instances of step 508' of FIG. 5B). For example, the electrode(s) which provided the most beneficial therapeutic effect may be selected. As another example, the electrode(s) that provided the most beneficial therapeutic effect with no side-effects (or with side-effects below a selected threshold) may be selected.

In step 512, responses are received for stimulations performed using the programming electrode(s) selected in step 510 at a series of different stimulation amplitudes.

In step 514, a programming stimulation amplitude is selected based on the responses received in step 512. Any criteria can be used for selecting the programming stimulation amplitude. For example, the stimulation amplitude that provided the most beneficial therapeutic effect with no side-effects (or with side-effects below a selected threshold) may be selected.

In some embodiments, steps 512 and 514 may be repeated for other stimulation parameters in place of stimulation amplitude. For example, in some embodiments, steps 512 and 514 may be repeated for pulse width instead of stimulation amplitude. In some embodiments, steps 512 and 514 may be repeated for pulse duration or pulse rate instead of stimulation amplitude. Any subset of additional stimulation parameters may be titrated and selected using the procedure of steps 512 and 514; typically, with previously selected stimulation parameters being held at their selected value.

In step 516, the system is directed to program the implantable pulse generator. In at least some embodiments, this direction may be automatic upon selecting the electrodes and stimulation amplitude (and, optionally, other stimulation parameter(s)). In some embodiments, the direction is made by a clinician, programmer, or other user.

In step 518, a signal is initiated by the system to program the implantable pulse generator with stimulation parameters including the programming electrode(s) and programming stimulation amplitude (and, optionally, other stimulation parameter(s)). The implantable pulse generator can then use this programming to stimulate the patient through the attached lead and electrodes.

Figure 6A:
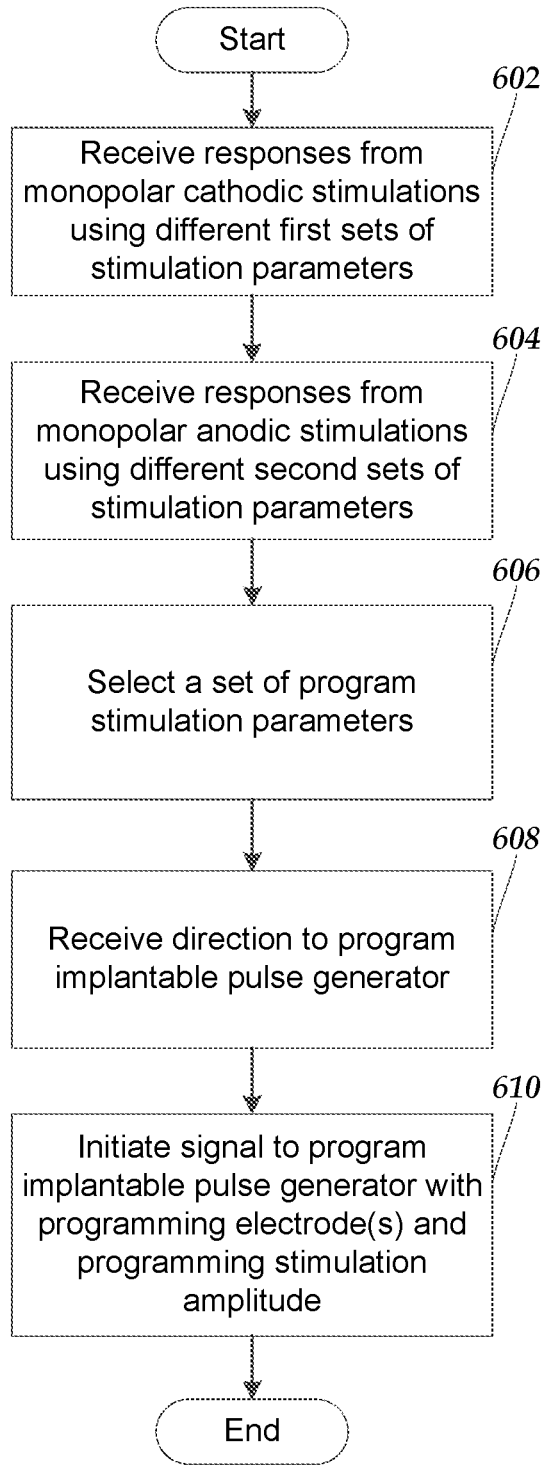
FIG. 6A is a flowchart of a third embodiment of a method for programming electrical stimulation of a patient.

FIG. 6A illustrates one method of selecting stimulation parameters for an electrical stimulation system. In step 602, responses are received for multiple monopolar cathodic stimulations performed using different first sets of stimulation parameters. Each of the cathodic stimulations uses a subset of one or more electrodes of a lead as a cathode as part of the first set of stimulation parameters. The responses to stimulation can be any quantitative or qualitative assessment of the stimulation itself, one or more therapeutic effects, or one or more side-effects, or any combination thereof. For example, the response may include a rating of the stimulation itself on a scale of numbers or qualitative scale (e.g., ineffective, good, poor, unacceptable). As another example, the response may include a rating of one or more beneficial therapeutic effects or side-effects on a scale of numbers or qualitative scale. If more than one effect is rated, the rating may be an overall rating or there may be multiple ratings for each effect. The response may be from the programmer or other clinician directing the stimulations or from the patient or from one or more sensors or other device that monitor the patient or from any combination of these sources.

In step 604, responses are received for multiple monopolar anodic stimulations performed using different second sets of stimulation parameters as part of the first set of stimulation parameters. Each of the anodic stimulations uses a subset of one or more electrodes of a lead as an anode. The responses may be assessed using the same or a different assessment as those in step 602.

The monopolar stimulations in steps 602 and 604 may be performed in any order and may be intermingled. For example, the monopolar stimulations in step 602 may be performed first followed by the monopolar stimulations in step 604. In another example, the monopolar stimulations in step 604 may be performed first followed by the monopolar stimulations in step 602. In yet another example, one or more monopolar stimulations in step 602 may be performed followed by one or more monopolar stimulations in step 604 followed by further monopolar stimulation(s) in step 602, and so on. For example, cathodic stimulation using a particular subset of one or more electrodes can be performed in step 602 followed by anodic stimulation using the same subset of one or more electrodes in step 604 and this pattern can be repeated for multiple different subsets of one or more electrodes.

Figure 6B:
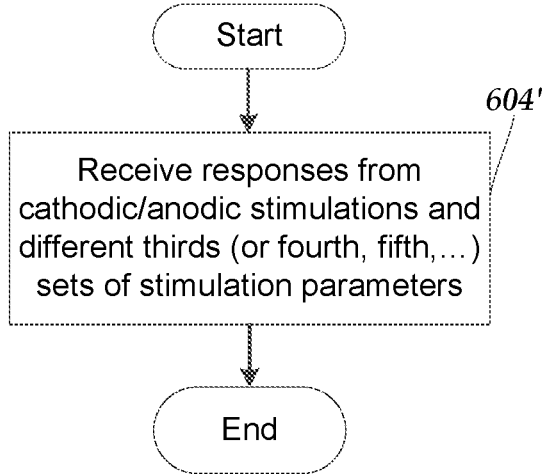
FIG. 6B is a flowchart of additional steps that can be added to the flowchart of FIG. 6A.

In some embodiments, the step 604' of FIG. 6B can be added one or more times after step 604. In step 604', responses are received for multiple bipolar or multipolar stimulations utilizing both anodic and cathodic stimulation (i.e., cathodic/anodic stimulation). For example, step 604' may be performed using a combination of 50% anodic and 50% cathodic stimulation, or 25% anodic and 75% cathodic, or any other combination. Step 604' may be performed one, two, three, four, or more times using different relative amounts of anodic and cathodic stimulation. It will be understood that that the relative strengths of anode and cathode on the lead can be different, and this may be accomplished by putting some current of one polarity at the case or housing of the IPG (or other distant location). The sum of the currents for a given polarity must be equal to the sum of the currents for the other polarity.

Returning to FIG. 6A, in step 606, one of the sets of first or second (or, optionally, third, fourth, fifth, . . . ) stimulation parameters is selected as a program set of stimulation parameters. Any criteria can be used for selecting between the sets of first or second (or, optionally, third, fourth, fifth, . . . ) stimulation parameters. For example, the set of stimulation parameters which provided the most beneficial therapeutic effect may be selected. As another example, the set of stimulation parameters that provided the most beneficial therapeutic effect with no side-effects (or with side-effects below a selected threshold) may be selected.

In step 608, the system is directed to program the implantable pulse generator. In at least some embodiments, this direction may be automatic upon selecting the set of program stimulation parameters. In some embodiments, the direction is made by a clinician, programmer, or other user.

In step 610, a signal is initiated by the system to program the implantable pulse generator with set of program stimulation parameters. The implantable pulse generator can then use this programming to stimulate the patient through the attached lead and electrodes.

During programming sessions, as well as at other times, it can be helpful to visualize the region that will be stimulated. Stimulation region visualization systems and methods can be used to predict or estimate a region of stimulation for a given set of stimulation parameters. In at least some embodiments, the systems and methods further permit a user to modify stimulation parameters and visually observe how such modifications can change the predicted or estimated stimulation region. Such algorithms and systems may provide greater ease of use and flexibility and may enable or enhance stimulation therapy. The terms "stimulation field map" (SFM), "volume of activation" (VOA), or "volume of tissue activated (VTA)" are often used to designate an estimated region of tissue that will be stimulated for a particular set of stimulation parameters. Any suitable method for determining the VOA/SFM/VTA can be used including those described in, for example, U.S. Pat. Nos. 8,326,433; 8,379,952; 8,649,845; 8,675,945; 8,831,731; 8,849,632; 8,855,773; 8,913,804; 8,918,183; 8,958,615; 9,026,317; 9,050,470; 9,072,905; 9,081,488; 9,084,896; 9,135,400; 9,235,685; 9,254,387; 9,227,074; 9,272,153; 9,302,110; 9,308,372; 9,310,985; 9,364,665; 9,526,902; 9,586,053; 9,792,412; 9,821,167; 9,925,382; and 9,959,940; U.S. Patent Application Publications Nos. 2009/0287272; 2009/0287273; 2012/0314924; 2013/0116744; 2014/0122379; and 2015/0066111; U.S. patent application Ser. Nos. 15/706,004 and 15/937,264; and U.S. Provisional Patent Applications Ser. Nos. 62/030,655 and 62/532,869, all of which are incorporated herein by reference in their entireties.

In at least some embodiments, as a precursor or during any of the methods described above (including those methods described using the flowcharts of FIGS. 4A to 6B), a set of stimulation parameters or a set of electrodes may be determined or suggested using a VOA/SFM/VTA visualization system. In at least some embodiments, a system, such as, for example, the system illustrated in FIG. 3, the CP 18 or RC 16 of FIG. 1, or any other suitable system or device, can be configured to determine, visualize, or otherwise use VOAs/SFMs/VTAs. In addition to the references cited above, other methods and systems for visualization of VOAs/SFMs/VTAs for anodic and cathodic stimulation are described in U.S. Provisional Patent Application No. 62/663,895 entitled "Systems and Methods for Visualizing and Programming Electrical Stimulation", filed on even date herewith, which is incorporated herein by reference in its entirety.

Figure 7:
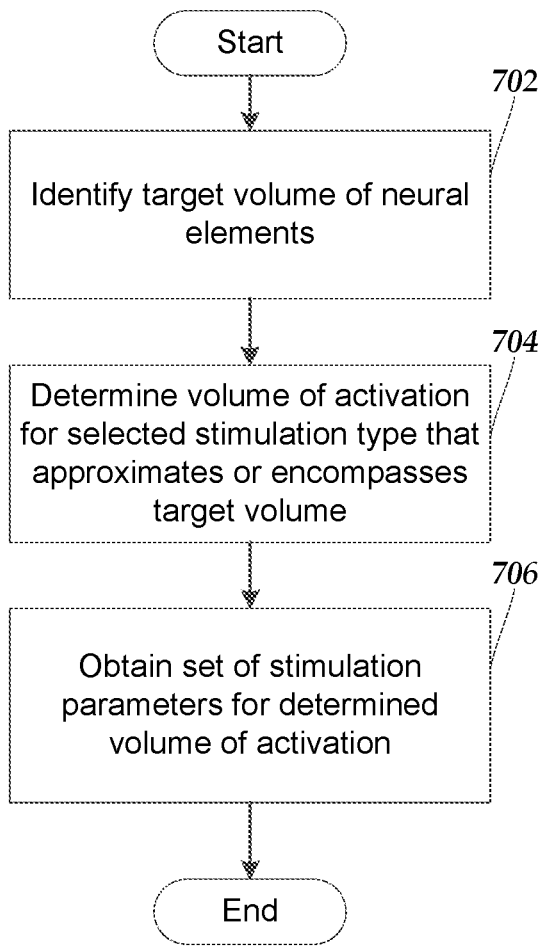
FIG. 7 is a flowchart of one embodiment of a method obtaining stimulation parameters that can be used in conjunction with the flowcharts of FIGS. 4A to 6B.

FIG. 7 is a flowchart of one embodiment of a method of determining or suggesting a set of stimulation parameters or electrodes. In step 702, a target volume of neural elements is identified. Any suitable method of identification can be used including, but not limited to, methods and systems described in any of the references cited above and U.S. Pat. Nos. 8,379,952; 8,649,845; 8,831,731; 8,855,773; 8,913,804; 8,918,183; 9,026,317; 9,050,470; 9,072,905; 9,081,488; 9,084,896; 9,135,400; 9,227,074; 9,235,685; 9,254,387; 9,272,153; 9,302,110; 9,308,372; 9,310,985; 9,364,665; 9,526,902; 9,586,053; 9,792,412; 9,821,167; 9,925,382; and 9,959,940; U.S. Patent Application Publications Nos. 2016/0375248; 2016/0375258; and 2017/0304633; U.S. patent application Ser. No. 15/706,004; 15/864,876; and 15/937,264; and U.S. Provisional Patent Applications Ser. Nos. 62/030,655 and 62/532,869, all of which are incorporated herein by reference in their entireties.

In step 704, a VOA (or SFM or VTA) is determined that approximates or encompasses the target volume (or at least a threshold amount of the target volume). In at least some embodiments, this determination is performed using a model for the selected type of stimulation (e.g., cathodic, anodic, cathodic/anodic, fiber, cell, or the like or any combination thereof). Any suitable method of determination of a VOA/SFM/VTA can be used including, but not limited to, methods and systems described in any of the references cited above and U.S. Pat. Nos. 8,326,433; 8,379,952; 8,649,845; 8,675, 945; 8,831,731; 8,849,632; 8,855,773; 8,913,804; 8,918, 183; 8,958,615; 9,026,317; 9,050,470; 9,072,905; 9,081, 488; 9,084,896; 9,135,400; 9,227,074; 9,235,685; 9,254, 387; 9,272,153; 9,302,110; 9,308,372; 9,310,985; 9,364, 665; 9,526,902; 9,586,053; 9,792,412; 9,821,167; 9,925, 382; and 9,959,940; U.S. Patent Application Publications Nos. 2009/0287272; 2009/0287273; 2012/0314924; 2013/0116744; 2014/0122379; 2015/0066111; 2016/0375248; 2016/0375258; and 2017/0304633; U.S. patent application Ser. Nos. 15/706,004; 15/864,876; and 15/937,264; and U.S. Provisional Patent Applications Ser. Nos. 62/030,655 and 62/532,869, all of which are incorporated herein by reference in their entireties.

In step 706, the set of stimulation parameters or set of one or more electrodes of the determined VOA/SFM/VTA is obtained. This set of stimulation parameters or set of one or more electrodes can then be used in the methods described above as one set to test or may be used as a starting point to produce multiple sets to test. In at least some embodiments, the method illustrated in FIG. 7 may be performed multiple times for different types of stimulation (e.g., cathodic, anodic, cathodic/anodic, fiber, cell, or the like or any combination thereof).

In at least some embodiments, it is useful to visually graph the stimulation effects (for example, one or more therapeutic effects or side-effects, or any combination thereof) or responses with respect to one or more stimulation parameters such as, for example, electrode selection, stimulation amplitude, or the like, or any combination thereof. Any suitable method and arrangement for graphing stimulation effects can be used including, but not limited to, methods, arrangements, and systems described in U.S. Pat. Nos. 9,227,074; 9,358,398; 9,474,903; 9,492,673; 9,643, 015; and 9,643,017; U.S. Patent Application Publications Nos. 2014/0277284 and 2017/0100593; U.S. patent application Ser. Nos. 15/631,964 and 15/920,153; and U.S. Provisional Patent Application Ser. No. 62/532,869, all of which are incorporated herein by reference in their entireties.

As an example, one embodiment of a graph includes a two- or three-dimensional graph with electrode location along one or two dimensions and stimulation amplitude along one or two dimensions. Examples can be found in U.S. Pat. Nos. 9,227,074; 9,358,398; 9,474,903; 9,492,673; 9,643,015; and 9,643,017; U.S. Patent Application Publications Nos. 2014/0277284 and 2017/0100593; U.S. patent application Ser. Nos. 15/631,964 and 15/920,153; and U.S. Provisional Patent Application Ser. No. 62/532,869, all of which are incorporated herein by reference in their entireties. In some embodiments, an inner circle represents the therapeutic effects and an outer ring represents the side-effects with a shading, color, or intensity of the inner circle or outer ring representing the score, value, or intensity of the effect. As a modification of this arrangement, for methods or systems evaluating both anodic or cathodic stimulation using the same electrode, a corresponding marker might include an inner circle and three concentric rings to represent the therapeutic effects of cathodic stimulation, therapeutic effects of anodic stimulation, side-effects of cathodic stimulation, and side-effects of anodic stimulation in any order. As another example of a modification, the inner circle and outer ring may be split in half with one half representing cathodic stimulation and the other half representing anodic stimulation.

In at least some embodiments, during any of the methods described above (including those methods described using the flowcharts of FIGS. 4A to 6B), a graph of responses to stimulation can be generated. In at least some embodiments, a system, such as, for example, the system illustrated in FIG. 3, the CP 18 or RC 16 of FIG. 1, or any other suitable system or device, can be configured to generate the graph.

Figure 8:
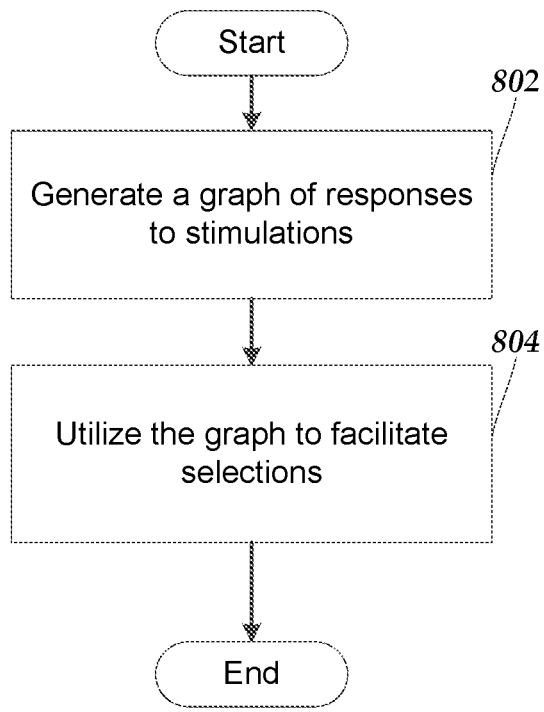
FIG. 8 is a flowchart of one embodiment of a method generate a graph of response to stimulations that can be used in conjunction with the flowcharts of FIGS. 4A to 6B.

FIG. 8 is a flowchart of one embodiment of a method of generating a using a graph of responses to stimulations. In step 802, a graph of responses to the stimulations is generated. Any suitable method, arrangement, or system can be used including, but not limited to, the methods, arrangements, and systems described above in the references cited above.

In step 804, the graph is used to facilitate selection of a set of one or more electrodes or set of stimulation parameters. The graph can provide a useful visualization of the responses to stimulation.

In at least some embodiments, any of the methods described herein, including the methods illustrated in FIGS. 4A to 6B, may be performed manually. In other embodiments, the methods may be performed using a semi- or wholly automated system. Example of methods for semi- or wholly automating adjustments to stimulation parameters of electrical stimulation systems can be found at, for example, the references cited above and U.S. Pat. No. 9,248,280; U.S. Patent Applications Publication Nos. 2016/0136429; 2016/0136443; and 2016/0256693; and U.S. patent application Ser. No. 15/783,961, all of which are incorporated herein by reference in their entireties. For example, the system may select electrodes and stimulation parameters in automatically or with some feedback from the patient or clinician. In some embodiments, the system may utilize one or more sensors to obtain the response to stimulation and utilize that responses in an automated system to select additional electrodes or stimulation parameters to try or in the selection steps of the methods described above. The optional sensors can be any suitable type of sensor including, but not limited to, optical sensors, piezoelectric sensors, chemical sensors, accelerometers, local field potential sensors, evoked compound action potential (eCAP) sensors, or the like. The sensors may be separate from the implantable pulse generator, lead, or other components of the system or may be disposed on the implantable pulse generator, lead, or other components of the system. The sensors may be identical or may be different (for example, different types of sensors or sensors for different types of chemicals or signals). In at least some embodiments, a sensor can be wire- or wirelessly coupled to an implantable pulse generator, CP, RC, or any other suitable device using wires, leads, Bluetooth™, rf transmission, or any other suitable transmission arrangement.

In some embodiments, the system may select electrodes or generate new stimulator parameter values using machine learning techniques or any other suitable methods including, but not limited to, gradient-descent, genetic algorithms, swarm algorithms, statistical algorithms, brute-force searching, or any of the methods described in U.S. patent application Ser. No. 15/783,961 or any of the other references cited above, all of which are incorporated by reference in their entirety.

The programming procedure performed in conventional electrical stimulation (such as deep brain or spinal cord stimulation) is often performed in an initial session and, in at least some instances, at later sessions. The methods described herein can be used in this manner.

In other embodiments, the methods described herein, including the methods illustrated in FIGS. 4A to 6B, can be used in an automated fashion in a feedback loop to monitor a patient and adjust stimulation parameters based on current patient responses. In some embodiments, the methods may be performed periodically; for example, every 1, 2, 4, 8, or 12 hours, or 1, 2, 4, or 7 days, or 2 or 4 weeks or 1 month or any other suitable time interval. In some embodiments, alternatively or additionally, the methods may be performed on user demand for a user such as the patient, clinician, or any other suitable individual. In other embodiments, the methods may be performed continually.

It will be understood that the system can include one or more of the methods described hereinabove with respect to FIGS. 4A to 8 in any combination. The methods, systems, and units described herein may be embodied in many different forms and should not be construed as limited to the embodiments set forth herein. Accordingly, the methods, systems, and units described herein may take the form of an entirely hardware embodiment, an entirely software embodiment or an embodiment combining software and hardware aspects. The methods described herein can be performed using any type of processor or any combination of processors where each processor performs at least part of the process.

It will be understood that each block of the flowchart illustrations, and combinations of blocks in the flowchart illustrations and methods disclosed herein, can be implemented by computer program instructions. These program instructions may be provided to a processor to produce a machine, such that the instructions, which execute on the processor, create means for implementing the actions specified in the flowchart block or blocks disclosed herein. The computer program instructions may be executed by a processor to cause a series of operational steps to be performed by the processor to produce a computer implemented process. The computer program instructions may also cause at least some of the operational steps to be performed in parallel. Moreover, some of the steps may also be performed across more than one processor, such as might arise in a multi-processor computer system. In addition, one or more processes may also be performed concurrently with other processes, or even in a different sequence than illustrated without departing from the scope or spirit of the invention.

The computer program instructions can be stored on any suitable computer-readable medium including, but not limited to, RAM, ROM, EEPROM, flash memory or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a computing device.

The above specification provides a description of the structure, manufacture, and use of the invention. Since many embodiments of the invention can be made without departing from the spirit and scope of the invention, the invention also resides in the claims hereinafter appended.

What is claimed as new and desired to be protected by Letters Patent of the United States is:

1. A system for programming electrical stimulation of a patient using an implantable electrical stimulation system comprising an implantable pulse generator and a lead having a plurality of electrodes, the system comprising:
a processor configured to:
receive a first response for each of a plurality of first stimulations performed using a plurality of different first subsets of one or more of the electrodes of the lead, wherein each of the first stimulations uses one of the first subsets and each of the first subsets is used for at least one of the first stimulations, wherein the first stimulations are each configured to preferentially stimulate a first type of neural element over a second type of neural element by selection of at least one of a first value of a stimulation amplitude, a first type of a stimulation polarity, a first value of a pulse width, a first value of a pulse rate, or a first value of a pulse duration for the first stimulation;
select a one of the first subsets of one or more of the electrodes based, at least in part, on the first responses;
receive a second response for each of a plurality of second stimulations performed using a plurality of different second subsets of one or more of the electrodes, wherein each of the second stimulations uses one of the second subsets and each of the second subsets is used for at least one of the second stimulations, wherein the second stimulations are configured to preferentially stimulate the second type of neural element over the first type of neural element by selection of at least one of a second value of the stimulation amplitude, a second type of the stimulation polarity, a second value of the pulse width, a second value of the pulse rate, or a second value of the pulse duration for the second stimulation;
select a one of the second subsets of one or more of the electrodes based, at least in part, on the second responses;
select a programming subset of one or more of the electrodes based on the first and second responses associated with the selected one of the first subsets and the selected one of the second subsets, respectively;
receive direction to program the implantable pulse generator with the programming subset of one or more of the electrodes; and
initiate a signal that provides the implantable pulse generator of the implantable electrical stimulation system with the programming subset of one or more of the electrodes for generating electrical stimulation for the patient through the electrodes of the lead.

2. The system of claim 1, wherein receiving a first response comprises receiving a first quantitative or qualitative indication of at least one therapeutic effect and receiving a second response comprises receiving a second quantitative or qualitative indication of at least one therapeutic effect.

3. The system of claim 1, wherein receiving the first response comprises receiving a first quantitative or qualitative indication of at least one therapeutic effect, at least one side-effect, or any combination thereof and receiving the second response comprises receiving a second quantitative or qualitative indication of at least one therapeutic effect, at least one side-effect, or any combination thereof.

4. The system of claim 3, wherein selecting the programming subset of one or more of the electrodes comprises selecting the programming subset of one or more of the electrodes based on the first and second quantitative or qualitative indications.

5. The system of claim 1, wherein the processor is further configured to:
receive a third response for each of a plurality of third stimulations performed using a plurality of different third subsets of one or more of the electrodes, wherein each of the third stimulations uses one of the third subsets and each of the third subsets is used for at least one of the third stimulations, wherein the third stimulations are configured to preferentially stimulate a third type of neural element over the first and second types of neural element by selection of at least one of a third value of the stimulation amplitude, a third type of the stimulation polarity, a third value of the pulse width, a third value of the pulse rate, or a third value of the pulse duration for the third stimulation; and
select a one of the third subsets of one or more of the electrodes based, at least in part, on the third responses;
wherein selecting the programming subset of one or more of the electrodes comprises selecting the programming subset of one or more of the electrodes based, at least in part, on the first responses, second responses, and third responses associated with the selected one of the first subsets, the selected one of the second subsets, and the selected one of the third subsets, respectively.

6. The system of claim 1, wherein receiving the first response comprising receiving the first response from a clinician, patient, or sensor.

7. The system of claim 1, wherein the first type of neural element and the second type of neural elements are different types of fibers.

8. The system of claim 1, wherein the first type of neural element and the second type of neural elements are different types of cells.

9. The system of claim 1, wherein the first type of neural element is large fibers and the second type of neural elements is small fibers that are smaller than the larger fibers.

10. The system of claim 1, wherein the first type of neural element is aligned, relative to the lead, along a first range of angles and the second type of neural elements is aligned, relative to the lead, along a second range of angles, wherein the first and second ranges do not overlap.

11. The system of claim 10, wherein the first type of neural element is aligned parallel to the lead and the second type of neural elements is aligned perpendicular to the lead.

12. The system of claim 1, wherein the first type of neural element is neural fibers and the second type of neural elements is neural cells that are not neural fibers.

13. The system of claim 1, wherein the first stimulations are monopolar cathodic stimulations and the second stimulations are monopolar anodic stimulations.

14. The system of claim 1, wherein, for each of the first subsets, the one or more of the electrodes of the first subset is the same as the one or more of the electrodes of a one of the second subsets.

15. A method for programming electrical stimulation of a patient using an implantable electrical stimulation system comprising an implantable pulse generator and a lead having a plurality of electrodes, the method comprising:
receiving a first response for each of a plurality of first stimulations performed using a plurality of different first subsets of one or more of the electrodes of the lead, wherein each of the first stimulations uses one of the first subsets and each of the first subsets is used for at least one of the first stimulations, wherein the first stimulations are each configured to preferentially stimulate a first type of neural element over a second type of neural element by selection of at least one of a first value of a stimulation amplitude, a first type of a stimulation polarity, a first value of a pulse width, a first value of a pulse rate, or a first value of a pulse duration for the first stimulation;
selecting a one of the first subsets of one or more of the electrodes based, at least in part, on the first responses;
receiving a second response for each of a plurality of second stimulations performed using a plurality of different second subsets of one or more of the electrodes, wherein each of the second stimulations uses one of the second subsets and each of the second subsets is used for at least one of the second stimulations, wherein the second stimulations are configured to preferentially stimulate the second type of neural element over the first type of neural element by selection of at least one of a second value of the stimulation amplitude, a second type of the stimulation polarity, a second value of the pulse width, a second value of the pulse rate, or a second value of the pulse duration for the second stimulation;
selecting a one of the second subsets of one or more of the electrodes based, at least in part, on the second responses;
selecting a programming subset of one or more of the electrodes based on the first and second responses associated with the selected one of the first subsets and the selected one of the second subsets, respectively;
receiving direction to program the implantable pulse generator with the programming subset of one or more of the electrodes; and
initiating a signal that provides the implantable pulse generator of the implantable electrical stimulation system with the programming subset of one or more of the electrodes for generating electrical stimulation for the patient through the electrodes of the lead.

16. The method of claim 15, wherein receiving a first response comprises receiving a first quantitative or qualitative indication of at least one therapeutic effect and receiving a second response comprises receiving a second quantitative or qualitative indication of at least one therapeutic effect.

17. The method of claim 15, wherein receiving the first response comprises receiving a first quantitative or qualitative indication of at least one therapeutic effect, at least one side-effect, or any combination thereof and receiving the second response comprises receiving a second quantitative or qualitative indication of at least one therapeutic effect, at least one side-effect, or any combination thereof.

18. The method of claim 17, wherein selecting the programming subset of one or more of the electrodes comprises selecting the programming subset of one or more of the electrodes based on the first and second quantitative or qualitative indications.

19. The method of claim 15, wherein the processor is further configured to:
receive a third response for each of a plurality of third stimulations performed using a plurality of different third subsets of one or more of the electrodes, wherein each of the third stimulations uses one of the third subsets and each of the third subsets is used for at least one of the third stimulations, wherein the third stimulations are configured to preferentially stimulate a third type of neural element over the first and second types of neural element by selection of at least one of a third value of the stimulation amplitude, a third type of the stimulation polarity, a third value of the pulse width, a third value of the pulse rate, or a third value of the pulse duration for the third stimulation; and select a one of the third subsets of one or more of the electrodes based, at least in part, on the third responses;

wherein selecting the programming subset of one or more of the electrodes comprises selecting the programming subset of one or more of the electrodes based, at least in part, on the first responses, second responses, and third responses associated with the selected one of the first subsets, the selected one of the second subsets, and the selected one of the third subsets, respectively.

20. The method of claim 15, wherein receiving the first response comprising receiving the first response from a clinician, patient, or sensor.

\* \* \* \* \*